(12) United States Patent
Zhang et al.

(10) Patent No.: US 8,895,302 B2
(45) Date of Patent: Nov. 25, 2014

(54) DIRECTED DIFFERENTIATION OF PRIMATE PLURIPOTENT STEM CELLS INTO FUNCTIONAL BASAL FOREBRAIN CHOLINERGIC NEURONS (BFCNS) AND MEDIUM SPINY GABAERGIC PROJECTION NEURONS

(75) Inventors: Su-Chun Zhang, Waunakee, WI (US); Yan Liu, Madison, WI (US); Lixiang Ma, Shanghai (CN)

(73) Assignee: Wisconsin Alumni Research Foundation, Madison, WI (US)

( * ) Notice: Subject to any disclaimer, the term of this patent is extended or adjusted under 35 U.S.C. 154(b) by 421 days.

(21) Appl. No.: 13/207,202

(22) Filed: Aug. 10, 2011

(65) Prior Publication Data

US 2012/0040393 A1    Feb. 16, 2012

Related U.S. Application Data

(60) Provisional application No. 61/401,374, filed on Aug. 12, 2010.

(51) Int. Cl.
*C12N 5/02* (2006.01)
*C12N 5/0793* (2010.01)
*G01N 33/50* (2006.01)

(52) U.S. Cl.
CPC .......... *C12N 5/0619* (2013.01); *C12N 2501/41* (2013.01); *C12N 2506/45* (2013.01); *C12N 2501/155* (2013.01); *C12N 2501/115* (2013.01); *C12N 2501/15* (2013.01); *C12N 2501/01* (2013.01); *C12N 2501/105* (2013.01); *C12N 2501/13* (2013.01); *C12N 2501/392* (2013.01); *C12N 2502/086* (2013.01); *C12N 2506/02* (2013.01); *C12N 2533/52* (2013.01); *G01N 33/5058* (2013.01); *G01N 2500/10* (2013.01)
USPC .......................................... 435/377; 435/385

(58) Field of Classification Search
CPC ............. C12N 2506/02; C12N 5/0619; C12N 2501/01; C12N 2501/105; C12N 2501/115; C12N 2501/13; C12N 2501/15; C12N 2501/155; C12N 2501/41; C12N 2506/45
See application file for complete search history.

(56) References Cited

U.S. PATENT DOCUMENTS

| 7,294,510 B2 * | 11/2007 | Okano et al. ............... 435/377 |
| 2008/0227137 A1 * | 9/2008 | Zhang et al. ............... 435/29 |

FOREIGN PATENT DOCUMENTS

WO    02/12333 A1 *    2/2002    ............... C12N 5/00

OTHER PUBLICATIONS

Benson et al. Characterization of GABAergic neurons in hippocampal cell culturesJournal of Neurocytology, 1994, vol. 23, pp. 279-295.*

Parmar et al.Phenotypic and molecular identity of cells in the adult subventricular zone: in vivo and after expansion in vitro Molec. Cellular Neuroscience, 2003, vol. 24, pp. 741-752.*

Mazzoni et al. Transforming growth factor a differentially affects GABAergic and cholinergic neurons in rat medial septal cell culturesBrain Research, 1996, vol. 707, pp. 88-99.*

Wu et al. Region-specific generation of cholinergic neurons from fetal human neural stem cells grafted in adult rat. Nature Neuroscience, 2002, vol. 5, pp. 1271-1278.*

Parmar et al.Phenotypic and molecular identity of cells in the adult subventricular zone: in vivo and after expansion in vitro. Molec. Cellular Neuroscience, 2003, vol. 24, pp. 741-752.*

Kallur et al. Human Fetal Cortical and Striatal Neural Stem Cells Generate Region-Specific Neurons In Vitro and Differentiate Extensively to Neurons After Intrastriatal Transplantation in Neonatal Rats. Journal of Neuroscience Research, 2006, vol. 84, pp. 1630-1644.*

Chalphin et al. The specification of glycinergic neurons and the role of glycinergic transmission in development. Frontiers in Molecular Neuroscience, 2010, vol. 3, pp. 1-13.*

Skogh et al. Generation of Regionally Specified Neurons in Expanded Glial Cultures Derived from the Mouse and Human Lateral Ganglionic Eminence. Molecular and Cellular Neuroscience, 2001, vol. 17, pp. 811-820.*

Elkabetz et al. Human ES cell-derived neural rosettes reveal a functionally distinct early neural stem cell stage Genes & Development, 2008, vol. 22, pp. 152-165.*

Backman, et al., Systemic Administration of a Nerve Growth Factor Conjugate Reverses Age-Related Cognitive Dysfunction and Prevents Cholinergic Neuron Atrophy, J. Neurosci., 1996, 16:5437-5442.

Berger-Sweeney, et al., Selective Immunolesions of Cholinergic Neurons in Mice: Effects on Neuroanatomy, Neurochemistry, and Behavior, J. Neurosci., 2001, 21:8164-8173.

Botly, et al., Cholinergic Deafferentation of the Neocortex Using 192 IgG-Saporin Impairs Feature Binding in Rats, J. Neurosci., 2009, 29:4120-4130.

Du, et al., NKX2.1 Specifies Cortical Interneuron Fate by Activating Lhx6, Development, 2008, 135:1559-1567.

Du, et al., Cre Recombination Mediated Cassette Exchange for Building Versatile Transgenic Human ESC Lines, Stem Cells, 2009, 27:1032-1041.

Flames, et al., Delineation of Multiple Subpallial Progenitor Domains by the Cominatorial Expression of Transcriptional Codes, J. Neurosci., 2007, 27:9682-9695.

Fragkouli, et al., LIM Homeodomain Transcription Factor-Dependent Specification of Bipotential MGE Progenitors Into Cholinergic and GABAergic Striatal Interneurons, Development, 2009, 136:3841-3851.

(Continued)

*Primary Examiner* — Deborah Crouch
(74) *Attorney, Agent, or Firm* — Quarles & Brady, LLP

(57) ABSTRACT

Methods of efficiently converting primate pluripotent stem cells to GABA neurons or cholinergic neurons, as well as applications thereof, are disclosed.

13 Claims, 10 Drawing Sheets
(10 of 10 Drawing Sheet(s) Filed in Color)

(56) References Cited

OTHER PUBLICATIONS

Furusho, et al., Involvement of the Olig2 Transcription Factor in Cholinergic Neuron Development of the Basal Forebrain, Dev. Biol., 2006, 293:348-357.

Gu, et al., Recombinant Human NGF-Loaded Microspheres Promote Survival of Basal Forebrain Cholinergic Neurons and Improve Memory Impairments of Spatial Learning in the Rat Model of Alzheimer's Disease with Fimbria-Fornix Lesion, Neurosci. Lett., 2009, 453:204-209.

Hartikka, et al., Development of Septal Cholinergic Neurons in Culture: Plating Density and Glial Cells Modulate Effects of NGF on Survival, Fiber Growth, and Expression of Transmitter-Specific Enzymes, J. Neurosci., 1988, 8:2967-2985.

Hu, et al., Differentiation of Spinal Motor Neurons from Pluripotent Human Stem Cells, Nat. Protoc., 2009, 4:1295-1304.

Johnson, et al., Functional Neural Development from Human Embryonic Stem Cells: Accelerated Synaptic Activity Via Astrocyte Coculture, J. Neurosci., 2007, 27:3069-3077.

Jordan, et al., Astrocytes Enhance Long-Term Survival of Cholinergic Neurons Differentiated from Human Fetal Neural Stem Cells, J. Neurosci. Res., 2008, 86:35-47.

Krencik, et al., Regional and Functional Specific Astrocytes from Human Embryonic Stem Cells, Society for Neuroscience Abstract, 2009, 808.9.

LaVaute, et al., Regulation of Neural Specification from Human Embryonic Stem Cells by BMP and FGF, Stem Cells, 2009, 27:1741-1749.

Lee, et al., Efficient Generation of Midbrain and Hindbrain Neurons from Mouse Embryonic Stem Cells, Nat. Biotechnol, 2000, 18:675-679.

Li, et al., Specification of Motoneurons from Human Embryonic Stem Cells, Nat. Biotechnol., 2005, 23:215-221.

Li, et al., Coordination of Sonic Hedgehog and Wnt Signaling Determines Ventral and Dorsal Telencephalic Neuron Types from Human Embryonic Stem Cells, Development, 2009, 136:4055-4063.

Manabe, et al., L3/Lhx8 is Involved in the Determination of Cholinergic or GABAergic Cell Fate, J. Neurochem., 2005, 94:723-730.

Manuel, et al., The Transcription Factor Foxg1 Regulates the Competence of Telencephalic Cells to Adopt Subpallial Fates in Mice, Development, 2010, 137:487-497.

Mesulam, et al., Central Cholinergic Pathways in the Rat: An Overview Based on an Alternative Nomenclature (Ch1-Ch6), Neuroscience, 1983, 10:1185-1201.

Perrier, et al., Derivation of Midbrain Dopamine Neurons from Human Embryonic Stem Cells, Proc. Natl. Acad. Sci. USA, 2004, 101:12543-12548.

Peterson, Quantitative Histology Using Confocal Microscopy: Implementation of Unbiased Stereology Procedures, Methods, 1999, 18:493-507.

Puelles, et al., Pallial and Subpallial Derivatives in the Embryonic Chick and Mouse Telencephalon, Traced by the Expression of the Genes Dlx-2, Emx-1, Nkx-2.1, Pax-6, and Tbr-1, J. Comp. Neurol., 2000, 424:409-438.

Reilly, et al., Cooperative Effects of Sonic Hedgehog and NGF on Basal Forebrain Cholinergic Neurons, Mol. Cell. Neurosci., 2002, 19:88-96.

Roy, et al., Functional Engraftment of Human ES Cell-Derived Dopaminergic Neurons Enriched by Coculture with Telomerase-Immortalized Midbrain Astrocytes, Nat. Med., 2006, 12:1259-1268.

Roy, et al., Enhancer-Specified GFP-Based FACS Purification of Human Spinal Motor Neurons from Embryonic Stem Cells, Exp., Neurol, 2005, 196:224-234.

Ullian, et al., Control of Synapse Number By Glia, Science, 2001, 291:657-661.

Walsh, et al., Injection of IgG 192-Saporin into the Medial Septum Produces Cholinergic Hypofunction and Dose-Dependent Working Memory Deficits, Brain Res., 1996, 726:69-79.

Wilson, et al., Induction and Dorsoventral Patterning of the Telencephalon, Neuron, 2000, 28:641-651.

Winkler, et al., Cholinergic Strategies for Alzheimer's Disease, J. Mol. Med., 1998, 76:555-567.

Winn, et al., Polymer-Encapsulated Genetically Modified Cells Continue to Secrete Human Nerve Growth Factor for Over One Year in Rat Ventricles: Behavioral and Anatomical Consequences, Exp. Neurol, 1996, 140:126-138.

Yan, et al., Directed Differentiation of Dopaminergic Neuronal Subtypes from Human Embryonic Stem Cells, Stem Cells, 2005, 23:781-790.

Yang, et al., Human Embryonic Stem Cell-Derived Dopaminergic Neurons Reverse Functional Deficit in Parkinsonian Rats, Stem Cells, 2008, 26:55-63.

Zhang, Neural Subtype Specification from Embryonic Stem Cells, Brain Pathol., 2006, 16:132-142.

Zhang, et al., In Vitro Differentiation of Transplantable Neural Precursors from Human Embryonic Stem Cells, Nat. Biotechnol., 2001, 19:1129-1133.

Zhao, et al., The LIM-Homeobox Gene Lhx8 is Required for the Development of Many Cholinergic Neurons in the Mouse Forebrain, Proc. Natl. Acad, Sci. USA, 2003, 100:9005-9010.

Gaspard et al., An intrinsic mechanism of corticogenesis from embryonic stem cells; Nature 455:351-357 (2008).

* cited by examiner

DIRECTED DIFFERENTIATION OF PRIMATE PLURIPOTENT STEM CELLS INTO FUNCTIONAL BASAL FOREBRAIN CHOLINERGIC NEURONS (BFCNS) AND MEDIUM SPINY GABAERGIC PROJECTION NEURONS

CROSS-REFERENCE TO RELATED APPLICATION

This application claims priority to U.S. Provisional Application 61/401,374 filed on Aug. 12, 2010, which is incorporated by reference herein.

STATEMENT REGARDING FEDERALLY SPONSORED RESEARCH OR DEVELOPMENT

N/A

BACKGROUND

Neurons in the ventral forebrain are critical to many neurological functions, including learning and memory, cognition, aggression, and movement. Degeneration or dysfunction of basal forebrain cholinergic neurons (BFCNs) underlies many neurological conditions, including Alzheimer's disease (AD), dementia, Korsakoff's disease, and progressive supranuclear palsy (Winkler et al., 1998). These disorders result in memory loss, impaired spatial recognition, and disturbance in language. Loss of another group of neurons in the ventral forebrain, medium spiny GABAeric (GABA) projection neurons in the striatum, underlies debilitating Huntington's disease (HD). Medium spiny GABA projection neurons are critical for coordinating movements. Patients with HD exhibit uncontrolled movements. At present, there are no effective treatment options for above diseases. Alternative therapies to protect and/or to replace the diseased neurons are urgently needed to combat these devastating diseases.

Availability of large quantity of BFCNs and medium spiny GABA projection neurons would enable the development of novel therapeutics. Many types of neural cells have been generated from self-renewing human embryonic stem cells (hESCs), cells capable of differentiating into all cell types of the human body (Zhang, 2006). Over the past decade, hESCs have been successfully differentiated to cerebral glutamatergic neurons (Li et al., 2009), midbrain dopaminergic neurons (Lee et al., 2000; Perrier et al., 2004; Yan et al., 2005), and spinal motoneurons (Li et al., 2005; Singh Roy et al., 2005). Importantly, some of these hESC-derived projection neurons have shown promise in improving behavioral deficits in animal models of diseases, including dopamine neurons in a rat model of Parkinson's disease (PD) (Roy et al., 2006; Yang et al., 2008). However, efficient differentiation of hESCs into BFCNs or medium spiny GABA projection neurons has yet to be achieved.

Needed in the art is a directed differentiation method in which primate pluripotent stem cells may be differentiated into functional BFCNs or medium spiny GABA projection neurons.

SUMMARY OF THE INVENTION

In one embodiment, the present invention is a method of creating a population of GABA neurons comprising the steps of differentiating primate pluripotent stem cells to primitive neural stem cells (Pax6+/Sox1−), exposing the primitive neural stem cells to SHH at 100-200 mg/ml or purmorphamine at 0.5-0.75 μM wherein GABA progenitors (Meis2$^+$/Gash2$^+$/Nkx2.1$^-$) are created, and differentiating the GABA progenitors into GABA neurons (GABA$^-$/DARPP32$^+$/Meis2$^+$). Preferably, the cells are human cells.

In one preferred embodiment, the efficiency of differentiation of the GABA neurons is at least 70%. More preferably, the efficiency is at least 80%.

In another embodiment, the present invention is a population of GABA$^+$/DARPP32$^+$/Meis2$^+$ GABA neurons produced by the method described above.

In yet another embodiment, the present invention is a method of creating a population of Meis2$^+$/Gash2$^+$/Nkx2.1$^-$ GABA progenitors comprising the steps of differentiating primate pluripotent stem cells to primitive neural stem cells (Pax6+/Sox1$^-$), and exposing the primitive neural stem cells to SHH at 100-200 mg/ml or purmorphamine at 0.5-0.75 μM wherein GABA progenitors (Meis2$^+$/Gash2$^+$/Nkx2.1$^-$) are created. Preferably, at least 80% of the total cells created are GABA progenitors. More preferably, at least 90% of the total cells created are GABA progenitors.

In yet another embodiment, the present invention is a population of GABA progenitors produced according to the method described in paragraph [0009]. Preferably, at least 80% of the population are GABA progenitors. More preferably, at least 90% of the population are GABA progenitors.

In another embodiment, the present invention is a method of creating a population of basal forebrain cholinergic neurons (BFCNs), comprising the steps of differentiating primate pluripotent stem cells into primate neural stem cells (Pax6+/Sox1$^-$), exposing the primate neural stem cells to SHH at 500-1000 mg/ml or purmorphamine at 1.0-1.25 μM, wherein cholinergic progenitors (Nkx2.1$^+$/Lhx8$^+$/Meis2$^-$) are formed, and differentiating the progenitors into BFCNs (ChAT$^+$/p75$^+$/Nkx2.1$^+$). Preferably, the cells are human cells. Preferably, the step of differentiating the progenitors into cholinergic neurons (ChAT$^+$/p75$^+$/Nkx2.1$^+$) is carried out in the presence of astrocytes.

In one preferred embodiment, the efficiency of differentiation of the BFCNs is at least 30%. More preferably, the efficiency is at least 40%.

In yet another embodiment, the present invention is a population of BFCNs produced by the method described in paragraphs [0011]-[0013].

In another embodiment, the present invention is a method of creating a population of Nkx2.1$^+$/Lhx8$^+$/Meis2$^-$ cholinergic progenitors comprising the steps of differentiating primate pluripotent stem cells into primate neural stem cells (Pax6+/Sox1$^-$), and exposing the primate neural stem cells to SHH at 500-1000 mg/ml or purmorphamine at 1.0-1.25 μM, wherein cholinergic progenitors (Nkx2.1$^+$/Lhx8$^+$/Meis2$^-$) are formed. Preferably, at least 90% of the cells created are cholinergic progenitors. More preferably, at least 95% of the cells created are cholinergic progenitors.

In another embodiment, the present invention is a population of Nkx2.1$^+$/Lhx8$^+$/Meis2$^-$ cholinergic progenitors created by the method described in paragraph [0014]. Preferably, at least 90% of the population are cholinergic progenitors. More preferably, at least 95% of the population are cholinergic progenitors.

BRIEF DESCRIPTION OF DRAWINGS

The patent or application file contains at least one drawing executed in color. Copies of this patent or patent application publication with color drawings will be provided by the Office upon request and payment of the necessary fee.

DESCRIPTION OF THE INVENTION

In General

Figure 1:
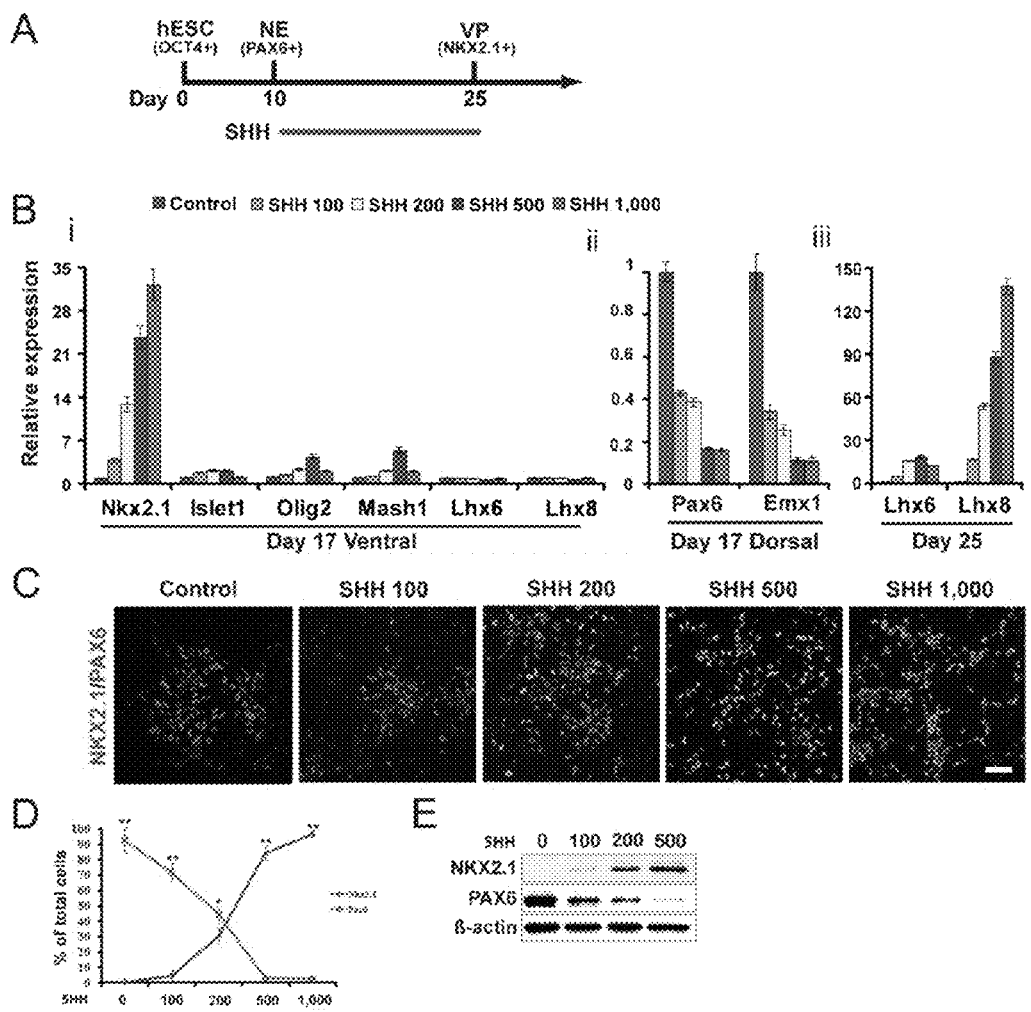
FIG. 1 shows the generation of telencephalic ventral progenitors from hESCs. (A) A schematic of the procedure for generating telencephalic ventral progenitors from hESCs by SHH. (B) RT-qPCR analysis indicated that at day 17 SHH repressed the expression of dorsal transcription factors Pax6 and Emx1 but increased the expression of ventral transcription factors Nkx2.1 and Mash1 in a dose-dependent manner. RTqPCR analysis by day 25 SHH induced the expression of GABAergic transcription factor Lhx6 at a lower SHH concentration and cholinergic transcription factor Lhx8 at higher SHH concentrations. (C, D and E) Immunocytochemistry, FACS, and Western blotting analysis showed downregulation of Pax6 and upregulation of Nkx2.1 in response to SHH. Bar=50 µm. (F) RT-qPCR analysis showed upregulated expression of Gsh2 and downregulation of Pax6 mRNA in the presence of SHH 200 and 0.65 uM of purmorphamine than control group by day 25. (G and H) Immunostaining showed increased expression of striatal GABA neuron progenitor markers Meis2, Mash1, and Otx2, decreased expression of cortical marker Pax6, and minimal expression of GABA interneuron progenitor marker Nkx2.1 in the presence of SHH 200 ng/ml or purmorphamine 0.65 uM at day 30. Bar=50 µm.*P<0.01.
Figure 1:
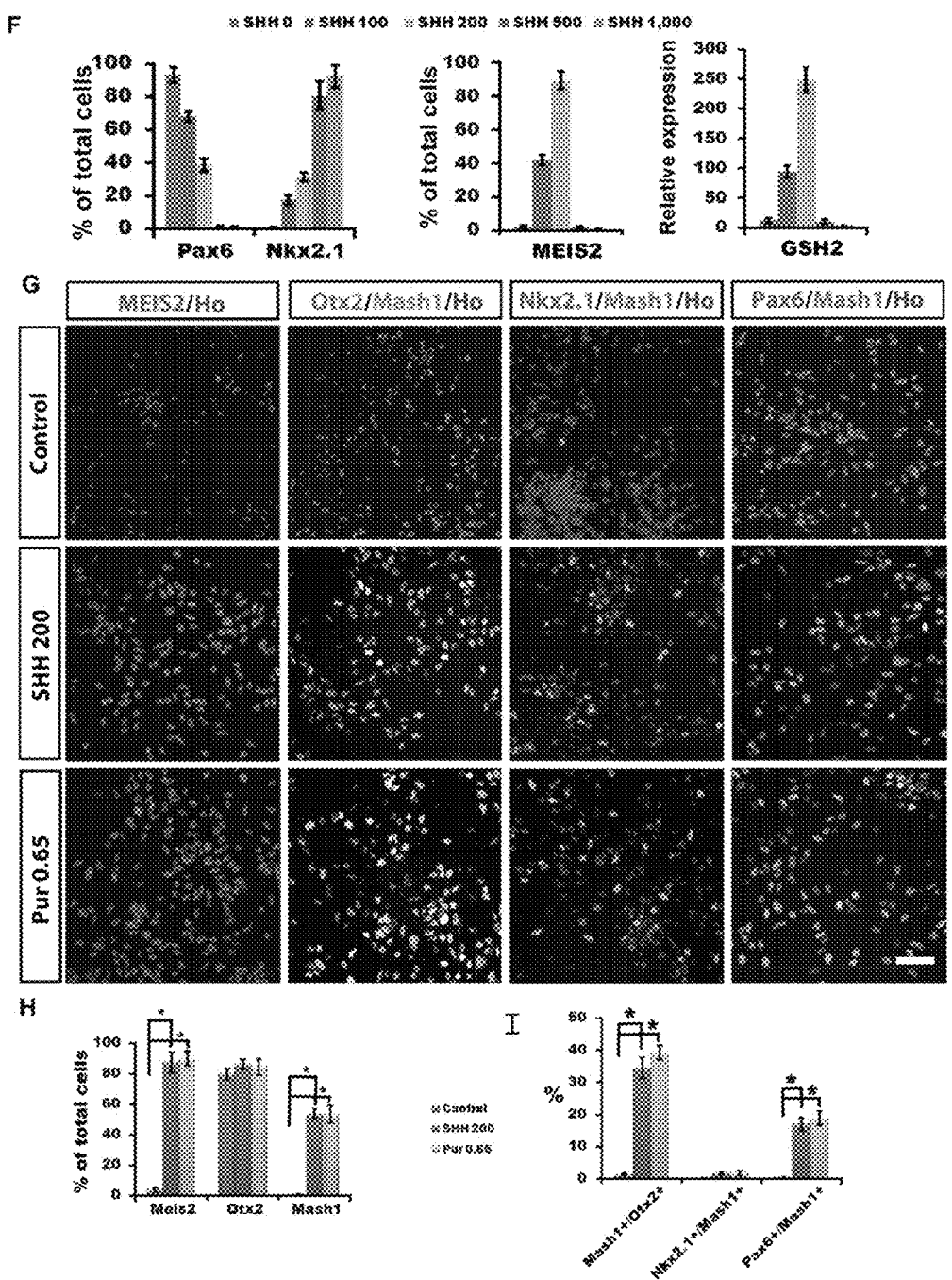

Cholinergic and GABA neurons are both derived from the ventral forebrain. Cholinergic neurons in the mammalian forebrain are located mainly in the medial septum (Ch1), diagonal band (Ch2, 3), and Nucleus Basalis of Meynert (Ch4) (Mesulam et al., 1983). The neurons project to the cerebral cortex, hippocampus and olfactory bulb, regulating learning, memory, and cognition.

Medium spiny GABA neurons are primarily located in the striatum. The neurons project to the thalamus and brain stem to regulate movement coordination.

During early embryonic development, the ventral forebrain is subdivided into two main domains in response to different concentrations of sonic hedgehong (SHH), the lateral ganglionic eminence (LGE) and the medial ganglionic eminence (MGE). Progenitors in the medial ganglionic eminence (MGE) and anterior entopeduncular area and preoptic area (AEP/POa) (Puelles et al., 2000; Wilson and Rubenstein, 2000), which express Nkx2.1, generate BFCNs and GABA interneurons. How the Nkx2.1 progenitors decide to become cholinergic neurons instead of other cell types (e.g., GABA) is not presently understood, although transcription factors, Lhx8 and 6, are thought to be involved (Du et al., 2008; Fragkouli et al., 2009; Zhao et al., 2003). Progenitors in the lateral ganglionic eminence (LGE), which express Gash2 and Meis2 but not Nkx2.1, produce medium spiny GABA projection neurons. Efficient conversion of Pluripotent Stem Cells to Medium Spiny GABA Projection Neurons or Basal Forebrain Cholinergic Neurons has not been achieved.

Degeneration of BFCNs has been implicated in neurological conditions that affect learning and memory, including Alzheimer's disease. Loss of medium spiny GABA projection neurons in the striatum or basal ganglia is a major course of Huntington's disease. The ability to direct pluripotent human stem cells, including ESCs and induced pluripotent stem cells (iPSCs) from patients such as Alzheimer's and Huntington's disease, would significantly facilitate dissection of cellular and molecular underpinnings of the disease pathologenesis. Practically, the BFCNS and medium spiny GABA neurons derived from Alzheimer's patients and Huntington's patients, respectively, may be utilized for drug discovery. Those generated from healthy individuals may be applied for cell replacement therapy as suggested by our transplant study shown in the present art.

Conversion of Pluripotent Stem Cells to Medium Spiny GABA Projection Neurons or Basal Forebrain Cholinergic Neurons The present application discloses the conversion of primate pluripotent stem cells, preferably hESCs or iPSCs, to a nearly homogeneous population of Nkx2.1-expressing, MGE and AEP/POa-like progenitors or Meis2-expressing LGE-like progenitors (see Scheme 1) by patterning the primitive neural stem cells with specific concentrations of SHH or purmorphamine. These progenitors yielded at least 30% BFCNs or 70% medium spiny GABA projection neurons. More preferably, the progenitors yielded at least 40% BFCNs or 80% medium spiny GABA projection neurons.

These in-vitro-produced BFCNs and medium spiny GABA projection neurons are different from the general spinal cholinergic and spinal GABA neurons in that, following transplantation into mice with loss of cholinergic or GABA neurons, the in-vitro-produced BFCNs and medium spiny GABA projection neurons corrected behavioral deficits of the mice (see Examples, below). In contrast, spinal GABA neurons did not contribute to function when transplanted into the striatrum. Similarly, spinal cholinergic neurons did not contribute to learning and memory recovery when transplanted into the hippocampus.

In one embodiment of the present invention, primate pluripotent stem cells, preferably human embryonic stem cells or human induced pluripotent stem cells, are differentiated into BFCNs through a cholinergic progenitor cell. For BFCN differentiation, the ESC-derived or iPSC-derived primitive neural stem cells are developed under SHH (500-1,000 ng/ml; 1845-SH; R&D System, MN, USA) or purmorphamine (1-1.25 uM) and are then treated with NGF (50-100 ng/ml; R&D) from day 24.

At day 28 the neural progenitors will adhere to laminin substrate or ESC-derived astrocytes (Krencik. R. et al., 2009) that were previously plated on the laminin at a density of 5,000 cells/cm$^2$. Astrocytes may be differentiated from ESCs, preferably according to a method described by Krencik (Krencik. R. et al., 2009). The plated cells are preferably grown in a neuronal differentiation medium consisting of neurobasal medium, N2 supplement (InVitrogen) in the presence of NGF (50-100 ng/ml; R&D), cAMP (1 μM; Sigma), BDNF, GDNF, IGFI, IGFII, BMP9, CNTF, and NT3 (10 ng/ml; R&D), SHH (50 ng/ml; R&D), estrogen (0.1 μg/ml; Sigma).

Differentiation of the cells into spinal cholinergic neurons may be performed according to a detailed protocol previously described (Hu and Zhang, 2009, incorporated by reference herein).

In another embodiment, the present invention is the creation of medium spiny GABA projection neurons from primate pluripotent stem cells. In a preferred embodiment, the stem cells are human ESCs or human iPSCs. For medium spiny GABA projection neuron differentiation, the ESC-derived or iPSC-derived primitive neural stem cells, generated under SHH (100-200 ng/ml) or purmorphamine (0.5-0.75 uM), will be cultured in the presence of valproic acid (VPA, 10 μM, Sigma) for 1 week, followed by trophic factors, such as brain derived neurotrophic factor (BDNF, 20 ng/ml), glial-derived neurotrophic factor (GDNF, 10 ng/ml), insulin-like growth factor 1 (IGF1, 10 ng/ml) and cAMP (1 μM) (all from R&D Systems).

Spinal GABA neurons may be differentiated, preferably according to a protocol detailed elsewhere (Hu et al., 2009, incorporated by reference herein).

Cholinergic Neuron Population

The Examples below show that primate pluripotent stem cells, specifically hESCs, are efficiently converted to primitive neural stem cells in a chemically defined medium in the first 10-12 days. By "primitive neural stem cell", we mean Pax6+/Sox1− cells that are characterized by early rosette morphology and have the full potential to differentiate into all types of neural cells in the body. Application of a high concentration (500-1000 ng/ml) of SHH for 7 to 14 days converts primitive neural stem cells to Nkx2.1-expressing MGE/AEP-like progenitors. Purmorphamine at 0.75-1.25 uM replaces SHH in converting primitive neural stem cells to MGE/AEP-like progenitors.

The cholinergic progenitors can be characterized as expressing Nkx2.1, Mash1, Lhx8, Lhx6, FoxG1, and Otx2 but not Pax6, Emx1, Meis2. The induction efficiency of cholinergic progenitors is at least 90%, preferably 95%. The inventors typically get 97±1.3%.

The cholinergic progenitors differentiate to mature BFCNs in the presence of astrocytes and neurotrophic factors. Our Examples show that the human BFCNs are at least twice the size of mouse cholinergic neurons. The BFCNs express Nkx2.1, Islett FoxG1, Tuj1, MAP2, neurofilament, ChAT, VAChT, P75, synapsin, and release acetylcholine. The BFCN differentiation efficiency is at least 30%, preferably 40%.

The BFCNs of the present invention are electrophyisiologically active and can functionally replace lost cholinergic neurons in mammals and improve learning, memory, and cognition. These BFCNs differ from spinal cholinergic neurons as spinal cholinergic neurons do not contribute to learning/memory and cognition.

In one embodiment, the present invention is a cell population wherein at least 40% of the cells are BFCNs. Preferably, the BFCNs are electrophysiolotgically active and can replace lost cholinergic neurons in mammals and improve learning memory or cognition.

Medium Spiny GABA Projection Neuron Population

In another embodiment, the present invention is a population of medium spiny GABA projection neurons. The Examples below show that primate pluripotent stem cells, specifically hESCs, are efficiently converted to primitive neural stem cells in a chemically defined medium in the first 10-12 days. Application of a specific concentration (100-200 ng/ml) of SHH for 7 to 14 days converted primitive neural stem cells to Meis2-expressing LGE-like progenitors. Purmorphamine at 0.5-0.75 uM replaces SHH in converting primitive neural stem cells to LGE-like progenitors.

The GABA progenitors express Meis2, Mash1, Gsh2, Dlx2, Pax6, FoxG1, and Otx2 but not Nkx2.1. The induction efficiency of Meis2-expressing GABA progenitors is at least 80%, most preferably, 90%.

The GABA progenitors differentiate to mature medium spiny GABA projection neurons in the presence of VPA and neurotrophic factors. The medium spiny GABA projection neurons of the present invention exhibit medium size with large and extensive dendritic trees packed with numerous fine spiny processes.

The human medium spiny GABA projection neurons express GABA, DARPP32, GAD65/67, FoxG1, Tuj1, MAP2, neurofilament, synapsin, and release GABA. The medium spiny GABA projection neurons differentiation efficiency is at least 70%, preferably 80%.

The human medium spiny GABA projection neurons are electrophyisiologically active. The human medium spiny GABA projection neurons can functionally replace lost GABA neurons in mammals and improve locomotion deficit. These medium spiny GABA projection neurons differ from spinal GABA neurons as spinal GABA neurons do not contribute to locomotion behavioral recovery in Huntington's mice.

EXAMPLES

Material and Methods

Culture of hESCs and Forebrain Cholinergic and GABAergic Neurons

Human ESCs (H9, passages 18-35; H1 passages 30-36) were maintained on a feeder layer of irradiated embryonic mouse fibroblast as previously described (Li et al., 2005). Differentiated colonies were removed physically and undifferentiated hESC state was confirmed by the uniform expression of OCT4, SSEA4, and NANOG.

The procedure for differentiating hESCs to neuroectodermal cells was the same as described (Li et al., 2005; Zhang et al., 2001). hESCs were differentiated to Pax6-expressing primitive neural stem cells for 10-12 days in a neural induction medium consisting of DMEM/F12, N2 supplement and non-essential amino acids (Pankratz et al., 2007; Zhang et al., 2001). The primitive neural stem cells were then treated with SHH (50-1000 ng/ml) or its small molecule agonist purmorphamine (0.1-1.5 uM, Calbiochem, San Diego, Calif., USA) from day 12 to day 26 to specify ventral progenitors. During this period, neural stem cells grew rapidly and formed neural tube-like rosettes, which were gently blown off at day 15-17 and grown in suspension under the same medium. For neuronal differentiation, neural progenitor clusters were dissociated with Accutase at 37° C. for 5 minutes and plated onto ornithine/laminin-coated coverslips at day 26 in Neurobasal medium.

For BFCN differentiation, the hESC-derived primitive neural stem cells under SHH (500-1,000 ng/ml; 1845-SH; R&D System, MN, USA) or purmorphamine (1-1.25 uM) were treated with NGF (50-100 ng/ml; R&D) from day 24. At day 28 the neural progenitors were adhered to laminin substrate or hESC-derived astrocytes (Krencik. R. et al., 2009) that were previously plated on the laminin at a density of 5,000 cells/cm$^2$. Astrocytes were differentiated from hESCs according to a method described by Krencik (Krencik. R. et al., 2009). The plated cells were grown in a neuronal differentiation medium consisting of neurobasal medium, N2 supplement (Invetrogen) in the presence of NGF (50-100 ng/ml; R&D), cAMP (1 μM; Sigma), BDNF, GDNF, IGFI, IGFII, BMP9, CNTF, and NT3 (10 ng/ml; R&D), SHH (50 ng/ml; R&D), Estrogen (0.1 μg/ml; Sigma). Differentiation of spinal cholinergic neurons was performed according to a detailed protocol previously described (Hu and Zhang, 2009, incorporated by reference).

For medium spiny GABA projection neuron differentiation, the hESC-derived neural progenitors, generated under SHH (100-200 ng/ml) or purmorphamine (0.5-0.75 uM), were cultured in the presence of Valproic acid (VPA, 10 μM, Sigma) for 1 week, followed by trophic factors, such as brain derived neurotrophic factor (BDNF, 20 ng/ml), glial-derived neurotrophic factor (GDNF, 10 ng/ml), insulin-like growth factor 1 (IGF1, 10 ng/ml) and cAMP (1 μM) (all from R&D Systems). Spinal motor neurons were differentiated according to a protocol detailed elsewhere (Hu et al., 2009).

Immunocytochemistry and Microscopy

Immunocytochemical staining on coverslip cultures and free-floating brain sections was performed as previously described (Li et al., 2005; Yang et al., 2008). The primary antibodies used in this study are as listed in Table 1. The images were visualized using a Nikon TE600 fluorescence microscope (Nikon Instruments, Melville, N.Y., USA) or a Nikon C1 laser-scanning confocal microscope.

TABLE 1

| Antibodies | | | |
|---|---|---|---|
| Antibody | Isotype | Dilution | Source |
| βIII-tubulin | Rabbit IgG | 1:10,000 | Covance Research Products |
| human nestin | Rabbit IgG | 1:500 | Chemicon & Millipore |
| Synapsin | Rabbit IgG | 1:1,000 | CALBIOCHEM |
| ChAT | Goat IgG | 1:300 | Chemicon & Millipore |
| VAChT | Rabbit IgG | 1:1,000 | Sigma |
| Human Nuclei | Mouse IgG | 1:200 | Chemicon & Millipore |
| P75 | Rabbit IgG | 1:500 | Chemicon & Millipore |
| PV | Rabbit IgG | 1:4,000 | Sigma |
| Tbr1 | Rabbit IgG | 1:5,000 | Chemicon & Millipore |
| Islet1 | Mouse IgG | 1:500 | DSHB, Iowa City, IA |
| GABA | Rabbit IgG | 1:10,000 | Sigma |

TABLE 1-continued

Antibodies

| Antibody | Isotype | Dilution | Source |
|---|---|---|---|
| Olig2 | Goat IgG | 1:400 | Santa Cruz |
| Nkx2.1 | Mouse IgG | 1:500 | Chemicon & Millipore |
| Pax6 | Rabbit IgG | 1:1,000 | Covance |
| Otx2 | Goat IgG | 1:500 | R&D system |
| Foxg1 | Rabbit IgG | 1:100 | Abcam |
| Mash1 | Mouse IgG | 1:500 | Neuromics |
| Ctip2 | Rabbit IgG | 1:400 | Chemicon & Millipore |
| HB9 | Mouse IgG | 1:50 | DSHB, Iowa City, IA |
| Hoxb4 | Rat IgG | 1:50 | DSHB, Iowa City, IA |
| Synaptophysin | Mouse IgG1 | 1:1000 | Chemicon & Millipore |
| Neurofilament 70 | Mouse IgG | 1:100 | Chemicon & Millipore |
| Meis 1/2 | Goat IgG | 1:500 | Santa Cruz |
| Ki67 | Rabbit IgG | 1:200 | ZYMED |
| GFAP | Rabbit IgG | 1:5,000 | DAKO |
| SOX2 | Goat IgG | 1:1,000 | R&D |
| Human Tau | Mouse IgG | 1:200 | ZYMED |
| VGLU | Rabbit IgG | 1:1,000 | Synaptic System |
| Mash1 | Mouse IgG1 | 1:500 | BD Pharmingen |
| GAD65/67 | Rabbit IgG | 1:5000 | Chemicon & Millipore |
| DARPP32 | Rabbit IgG | 1:1000 | Chemicon & Millipore |
| CTIP2 | Rat IgG | 1:5000 | Chemicon & Millipore |
| Synaptobrevin | Mouse IgG | 1:250 | Chemicon & Millipore |

Real-Time PCR

Total RNA was extracted using Trizol reagent (Invitrogen), and cDNA was reverse-transcribed using the SuperScript III First-Strand (Invitrogen). Real-time PCR was performed using the Bio-Rad MyiQ real-time PCR detection system as described (Du et al., 2009). Primers used were listed in Table 2.

TABLE 2

Primers (5' to 3') for real-time PCR

| Human gene | Forward | Reverse |
|---|---|---|
| Emx1 | TTCAATGGGAGAGGGAGAGT GCTT (SEQ ID NO: 1) | CCGTCAGCCTTTGTGAATGG TGTT ( SEQ ID NO: 2) |
| Lhx6 | ACAGATCTACGCCAGCGACT (SEQ ID NO: 3) | CATGGTGTCGTAGTGGATGC (SEQ ID NO: 4) |
| Mash1 | GTCTCCCGGGGATTTTGTAT (SEQ ID NO: 5) | TCTCCATCTTGGCAGAGCTT (SEQ ID NO: 6) |
| Lhx8 | CCAAAACCAGCAAAAAGAGC (SEQ ID NO: 7) | TGGCGTGCTCTACAATTCTG (SEQ ID NO: 8) |
| Islet1 | GTTTGAAATGTGCGGAGTGT AAT (SEQ ID NO: 9) | TTCTTGCTGAAGCCGATGC (SEQ ID NO: 10) |
| Nkx2.1 | CGCATCCAATCTCAAGGAAT (SEQ ID NO: 11) | CAGAGTGTGCCCAGAGTGAA (SEQ ID NO: 12) |
| Pax6 | TCTTTGCTTGGGAAATCCG (SEQ ID NO: 13) | CTGCCCGTTCAACATCCTTA G (SEQ ID NO: 14) |
| Olig2 | GGTAAGTGCGCAATGCTAAG CTGT (SEQ ID NO: 15) | TACAAAGCCCAGTTTGCAAC GCAG (SEQ ID NO: 16) |
| GAPDH | TCGACAGTCAGCCGCATCTT CTTT (SEQ ID NO: 17) | ACCAAATCCGTTGACTCCGA CCTT (SEQ ID NO: 18) |
| DIx2 | ATGTCGCTCCTTCTATGTC (SEQ ID NO: 19) | TCACTATCCGAATTTCAGGC TCA (SEQ ID NO: 20) |
| Gsh2 | ATGTCGCGCTCCTTCTATGT C (SEQ ID NO: 21) | ATGCCAAGCGGGATGAAGAA A (SEQ ID NO: 22) |

Determination of GABA or Acetylcholine Release by HPLC

For measurement of transmitters released by cultured neurons by HPLC, cultured cells were washed four times with Krebs'-Ringer's solution containing 130 mM NaCl, 3 mM KCl, 2 mM $CaCl_2$, 0.8 mM $MgSO_4$, 10 mM glucose, and 20 mM HEPES (pH 7.4). Depolarizing Krebs'-Ringer's solution contained 83 mM NaCl, 50 mM KCl, 2 mM $CaCl_2$, 0.8 mM $MgSO_4$, 10 mM glucose, and 20 mM HEPES (pH 7.4). Collected media were mixed with o-phthalaldehyde (0.8 g/L) and 2-mercaptoethanol (2 ml/L) for 5 min at 15 C. Samples were then injected into the HPLC system and analyzed using a fluorescence monitor (excitation at 350 nm, emission at 450 nm) (CMA/Microdialysis, Stockholm, Sweden) (Lindroth and Mopper, 1979). The mobile (60 μl/min) solution consisting of (in mM) 100 KH2PO4, 100 Na2HPO4, and 0.1 EDTA, pH6.0, contained 10% acetonitrile and 3% tetrahydrofuran. The peak area at the predicted position was calibrated against the standard curves for quantification with CMA200 software (CMA/Microdialysis).

Whole Cell Patch Clamp Recording

Whole-cell patch-clamp recordings were made from hESC-derived cholinergic neurons at 8-10 weeks age as previously reported (Johnson et al., 2007). Briefly, the neurons were held at −70 mV to record the spontaneous release and Na+/K+ channel activities. For action potential recording, the cells were held at 0 pA with current-clamp model and the steps of currents from +20 nA to +80 nA were injected into cells by the holding electrode. The bath solution consisted of 127 mM NaCl, 1.2 mM $KH_2PO_4$, 1.9 mM KCl, 26 mM $NaHCO_3$, 2.2 mM $CaCl_2$, 1.4 mM $MgSO_4$, 10 mM glucose, 290 mM mOsm and 95% O2/5% CO2. Recording pipettes were filled with an intracellular recording solution consisting of 20 mM KCl, 121 mM $K^+$-gluconate, 10 mM $Na^+$-HEPES, 10 mM BAPTA, 4 mM $Mg_2^+$-ATP pH 7.2 and 290 mOm. Bicuculline (20 μM; Sigma) or 6-cyano-7-nitroquinoxiline-2,3-dione (CNQX, 20 μM; RBI) was applied to the bath solution to distinguish inhibitory (GABAergic) and excitatory (glutamatergic) response. Biocytin (1%, Sigma) was injected into cells after recording to identify the neuronal identity. An Olympus BX51WI microscope was used to visualize neurons. A MultiClamp 700B amplifier (Axon instruments, Molecular Devices, Sunnyvale, Calif., USA) was used to investigate the voltage clamp and current clamp recordings. Signals were filtered at 4 kHZ and sampled at 100 kHz using a Digidata 1322A analog-digital converter (Axon instruments). Data were analyzed with pClamp 9.0 (Axon instruments). Data were presented as mean±s.e.m.

Western Blot

Protein samples were collected at day 25 after differentiation. Western blot analysis was performed as described (Li et al., 2009). Proteins (25 μg) were separated by 10% acrylamide gel and blotted with antibodies against Nkx2.1 (1:2,000, Mouse IgG, Chemicon & Millipore), Pax6 (1:4,000, Rabbit IgG, Covance), and β-actin (1:4,000, Mouse IgG, Sigma).

Disease Models and Cell Transplant

Severe combined immunodeficiency (SCID) male mice (8-10 weeks of age) were used in the experiments. The animal experiments, including behavioral tests, were carried out follow the protocols approved by the University of Wisconsin-Madison Animal Care and Use Committee.

Medial Septum Immunolesion and Cell Transplant

Mice were anesthetized with 1% isoflurane mixed with oxygen, and 0.8 μl anti-murine-p75-SAP (Berger-Sweeney et al., 2001) (Advanced Targeting System, San Diego, Calif.) was injected into the medial septum over a 5-minute period with a 15°-angle at the following stereotaxic coordinates: anterior-posterior (AP)=+0.38 mm; left lateral (L)=+1 mm;

and dorso-ventral (DV)=−4.12 mm. Two weeks after surgery, mice were subjected to Morris water maze (Nodule) tests. A total of 30 mice with learning and memory deficit and 10 sham operated mice which were injected with artificial cerebrospinal fluid (aCSF, Harvard apparatus, MA) were selected for subsequent experiments.

Six weeks after lesion, the affected mice were sub-divided into three groups, one group received transplantation with hESC-derived BFCNs, one with hESC-derived cholinergic spinal motor neurons, and the other with aCSF. Cells or CSF were injected into CA3 of hippocampus at the following stereotaxic coordinates: anterior-posterior (AP)=−2.46 mm; left-right lateral (LR)=±2 mm; and dorso-ventral (DV)=−2.25 mm. About 100,000 cells were injected into each side of the hippocampus in 2 μl over a 5-min period. Morris water maze was performed 2, 4, and 6 months after transplantation, and other behavioral tests, including visible platform Morris water maze, open field, pre-pulse inhibition, and passive avoidance, were carried out at 6 months post transplantation.

Striatal Lesions and Cell Transplantation

Twenty-four male SCID mice (10 weeks of age) were anesthetized with 1-2% isoflurane mixed in oxygen, and received stereotaxic injection of 2 μl 0.1M quinolinic acid (QA, P63204; Sigma, in saline with 0.2 mg/ml ascorbic acid) in the right striatum at the coordinates (anterior-posterior (AP)=−0.7 mm, lateral (L)=+1.7 mm, vertical (V)=−3.2 mm) to create the unilateral lesion (Hansson et al., 1999).

Differentiated striatal GABAergic neurons as well as spinal neurons (40 days from hESCs) were dissociated with Accutase. Cells were prepared at approximately 50,000 cells/ul artificial cerebrospinal fluid containing B27, 200 mM ascorbic acid, 1 mM cAMP, 20 ng/ml BDNF, and 10 ng/ml GDNF. Two microliters of cells was transplanted into the lesioned striatum (AP=−0.8 mm, L=+2.0 mm, V=−3.2 mm from the Bregma) of anesthetized animals (4 weeks after successful lesion) using a glass pipette (0.3-0.5 mm in diameter) over a period of 5 minutes. Control animals received the same surgery and injection of 2 ul of diluting solution.

Behavioral Tests

Behavioral tests were conducted before and after transplantation monthly until the animals were sacrificed.

Morris Water Maze

Morris water maze testing was performed 2 weeks after lesion, and 2, 4, and 6 months after cell transplantation. The swimming tank (130 cm diameter) was divided into 4 quarters with an escape platform hidden 0.5-1 cm underneath opac water (22±2° C.). The swimming behavior of mice was monitored by an automated video system. Mice were pretrained to locate the platform without data recording. The mice were trained for 4 consecutive days to reach the hidden platform. There were 2 blocks of four 60-second trials (8 total) each day, with 30 minutes of interval between the blocks. For the training trials, the latency to find the platform was recorded. After completion the 32 trials over 4 days, the hidden platform was removed, and one 60-second probe trial was conducted. For the probe trial, the number of "platform" crosses and the time spent in each quadrant were recorded.

In order to test the vision ability of the experimental mice, visible water maze was performed for 2 consecutive days (4 blocks totally) after the $6^{th}$ month water maze. The visible platform which was 5 cm above water surface with a black cubic (5×5×5 cm) was placed randomly in different quadrant in every single training. The latency to find the visible platform was recorded. Two-way ANOVAs with repeated measured were performed to analyze regular water maze, and one-way ANOVA was performed to analyze visible platform water maze.

Open Field

Open field testing was performed 6 months after transplantation. The open field arena (37 cm×37 cm, and 26 cm high) was divided into 16 grids (4×4). There are 4 grids in the center and 12 grids near the walls. A mouse was placed in the center of the container at the beginning, and a digital camera attached to a National Instruments® video on top monitored the behavioral of the mouse for 30 minutes. Coulbourn Instruments (Whitehall, Pa., USA) LimeLight2 software was used to record video and data which were captured 4 images per second (4 hz). Path data (x and y coordinates of tracked mouse) were exported into Excel® for analyses. One-way ANOVA was performed to analyze the open field data. All the tests were conducted at room temperature.

Passive Avoidance

Passive avoidance, which tests for learning to avoid aversive stimulation, was tested 6 months after transplantation. Because mice prefer a dark place, when they are placed in an apparatus with a light box and a dark box connected they move into the dark box. However, when a mouse is given an electric shock through the floor of the dark box (2-second 0.5 mA), the mouse hesitates to move into the dark box. The reason why the mouse hesitates to move into the dark box seems due to learning and memory. The latency to enter the dark box was measured before and 24 hours after the electric shock. One-way ANOVA was performed to compare the passive avoidance data of the experimental groups.

Apomorphine-Induced Rotation Test

At 7 days post-QA lesions, animals were injected with apomorphine (A4393, Sigma; 0.5 mg/kg in normal saline containing 0.2% ascorbate) and then placed in individual rotometer box for a 5 min habituation period before a 30 min test session. The rotation was recorded by a computer. The number of complete 360° turns was used in this study. The test was carried out monthly up to 5 months, including before and after 1, 2, 3, 4, and 5 months of transplantation.

Gait Movement by Treadmill Test

Huntington's disease patients exhibit uncoordinated locomotion. To develop behavioral tests that identify defects in animal models that resemble HD, we utilized a computerized treadmill device, TreadScanR (Columbus Instruments (Columbus, Ohio, USA) to detect gait movements. All mice were allowed to walk on the motor-driven treadmill belt at a speed of 15 cm/s for 20 s periods. A high-speed digital video camera was mounted to record the ventral view of the treadmill belt reflected off the mirror. TreadScan software (CleverSys) was used to identify initial foot contact, stance duration, stride duration, foot liftoff, swing duration, stride length, track width, and toe spread data for each foot. This test was carried out prior to transplantation and monthly up to 5 months post transplantation.

Rota-Rod Test

Mice were tested for motor endurance on an accelerating Rotarod (Columbus Instruments, Columbus, Ohio, USA). It is used to test motor coordination. Each mouse was trained three times and then recorded 5 runs as one trial. The mouse was placed on a rotating rod that accelerated from 4 rotations per minute (rpm) to 40 rpm in 300 s. The amount of time the mouse is on the rod was monitored and compared between experimental groups.

Cellular Quantification of Cultures and Histological Analysis of Transplants

To quantify the differentiation efficiency of forebrain progenitors, neural progenitor spheres were dissociated into single cells and quantified by fluorescent activated cell sorting (FACS) (LaVaute et al., 2009). For quantifying differentiated cholinergic neurons, the neural progenitor spheres were digested with Accutase (Innovation Cell Technology) into small clusters and plated on coverslips for immunostaining as previous described (Li et al., 2005; Hu et al., 2009). Optical fields of cultures were randomly selected, and the neuronal cells and total cells (Hoechst stained) were counted using a Metamorph software. All the experiments were triplicated and the results were reproduced in two different cell lines (H1 and H9). For statistical analysis, 2-side t-test was used.

At the end of the transplant experiments, the animals were perfused with 4% paraformaldehyde. After 4 hours of post-fixation, the brain was serially sectioned coronaly to 30 um in thickness. Total grafted human cells (hNu+) and cholinergic neurons (CHAT+/hNu+) or GABA neurons (GABA+/DARPP32+/hNu+) were counted on every 6 sections as described (Yang et al., 2008), using a Stereo Investigator software (MicroBrightField, Inc). The graft area was outlined according to the presence of hNu positive cells under a 10× objective of a fluorescent scope. Cell counts were performed under a 40× objective of a Zeiss fluorescent scope in fields chosen by the software. The total cells on each section and in the whole graft were estimated by the Stereo Investigator software (Peterson et al., 1999).

Results

Cholinergic and GABA Neuron Progenitors are Efficiently Induced from hESCs by SHH or Purmorphamine Human ESCs differentiate to multipotent primitive neural stem cells (pNSCs) at around day 8-15 (Pankratz et al., 2007), which generate predominantly dorsal telencephalic progenitors in the absence of exogenous morphogens due to overriding roles of endogenous wnts over SHH signaling (Li et al., 2009). We hypothesize that addition of exogenous SHH would pattern the pNSCs to ventral forebrain progenitors.

hESCs were first differentiated to Pax6-expressing pNSCs in a chemically defined medium as previously described (Johnson et al., 2007; Li et al., 2005; Zhang et al., 2001). We first determined the time course of SHH action by applying SHH for a week at day 10, 13, and 17 and by quantifying cells that express Nkx2.1, an MGE transcription factor. Consistent with our previous findings on patterning for midbrain dopamine neurons (Yan et al., 2005) and spinal motor neurons (Li et al., 2005), addition of SHH at day 10 resulted in the most efficient induction of Nkx2.1-expressing ventral telencephalic progenitors (FIG. 1A).

Basal forebrain cholinergic neurons (BFCNs) are differentiated from progenitors in the MGE and POa/AEP domains that express Nkx2.1 (Wilson and Rubenstein, 2000; Zhao et al., 2003). We then determined the most effective dosage of SHH to ventralize the neural stem cells by applying 0, 100, 200, 500, and 1,000 ng/ml SHH into the culture medium at day 10 and by assessing gene expression using quantitative PCR at day 17 and immunocytochemistry at day 25 (FIG. 1A). Results indicated that Nkx2.1 mRNA levels increased in response to increasing SHH concentrations in a dose-dependent manner. Expression of Mash1, Olig2, and Islett transcription factors expressed in both LGE and MGE cells (Flames et al., 2007; Furusho et al., 2006; Manuel et al., 2010), was also augmented although at a higher SHH concentration (1000 ng/ml) they were upregulated to a lesser degree (FIG. 1B). In contrast, the expression of dorsal telencephalic transcription factors, Pax6 and Emx1, was decreased (FIG. 1B). Immunostaining and Western blotting analyses confirmed that Nkx2.1-expressing cell population increased progressively, with 97±1.3% of the cells being Nkx2.1 positive in the presence of 1000 ng/ml of SHH, whereas the population of Pax6 positive dorsal progenitors decreased, to less than 0.01% under 1000 ng/mlof SHH (FIG. 1C, D, E). These results suggest that high concentration (500-1000 ng/ml) SHH can efficiently ventralize neural stem cells to ventral progenitors with an MGE and POa/AEP-like phenotype.

Lhx8 and, to a lesser degree, Lhx6 are implicated in the specification of the cholinergic fate in the basal forebrain (Fragkouli et al., 2009; Manabe et al., 2005; Zhao et al., 2003). RT-PCR analysis indicated that the expression of these two genes was not altered in the neural stem cells at day 17. However, their expression, especially that of Lhx8, was significantly increased in response to higher concentrations of SHH at day 25 (FIG. 1B). In contrast, Meis2, a transcription factor expressed by progenitors and neurons in LGE, was highly expressed in the presence of low concentration (100 ng/ml) SHH, but it was nearly completely blocked by high concentration (500 ng/ml) of SHH, as shown by immunostaining (FIG. 1F). Together, these results suggest that high dosages of SHH can effectively pattern hESC-derived primitive neural stem cells into MGE and POa/AEP-like progenitors.

Medium spiny GABA projection neurons develop primarily from lateral ganglionic eminence (LGE) progenitors (Olsson et al., 1995, 1997, 1998; Wichterle et al., 1999, 2001). These progenitors express MEIS2, Mash1 and, to a lesser degree, Pax6 but not Nkx2.1 (Fode et al., 2000 Toresson et al., 2000; Skogh et al., 2003). As shown in FIG. 1G, SHH at around 200 ng/ml, is optimal for reducing the Pax6-expressing cells to 40% and increasing Mash 1 positive cells to 50% yet minimally elevating Nkx2.1 population (20%) (FIG. 1G, H, I). Indeed, Meis2, a transcription factor that is enriched in striatal GABAergic progenitors (Parmar et al., 2002), was highly induced by 200 ng/ml SHH (FIG. 1G, H, I). mRNAs of Gsh2 and Dlx2, transcription factors expressed primarily in the LGE (Toresson 2000; Toresson and Campbell, 2001; Yun et al., 2001), increased drastically (FIG. 1F). Immunostaining also showed that a substantial population (20%) of progenitors co-expressed Mash1 and Pax6 (FIG. 1I).

We have previously shown that the activity of SHH may be replaced by a small molecule, purmorphamine (Li et al., 2005). Treatment of pNSCs at day 10-12 with purmophamine (0, 0.5, 0.75, 1.0, 1.25, 1.5 µM) resulted in a similar pattern of dorsal (Pax6) and ventral (Mash1, Nkx2.1) gene expression, and purmorphamine at 1 µM appeared equivalent to SHH at 500 ng/ml for cholinergic progenitors and purmorphamine at 0.65 uM seemed equivalent to SHH at 200 ng/ml for GABAergic progenitors (FIG. 1G, H, I). We therefore also used purmorphamine (1.25 uM, or 0.65 uM) for generating cholinergic and GABAergic progenitors.

Basal Forebrain Progenitors Generate Cholinergic Neurons

Figure 2:
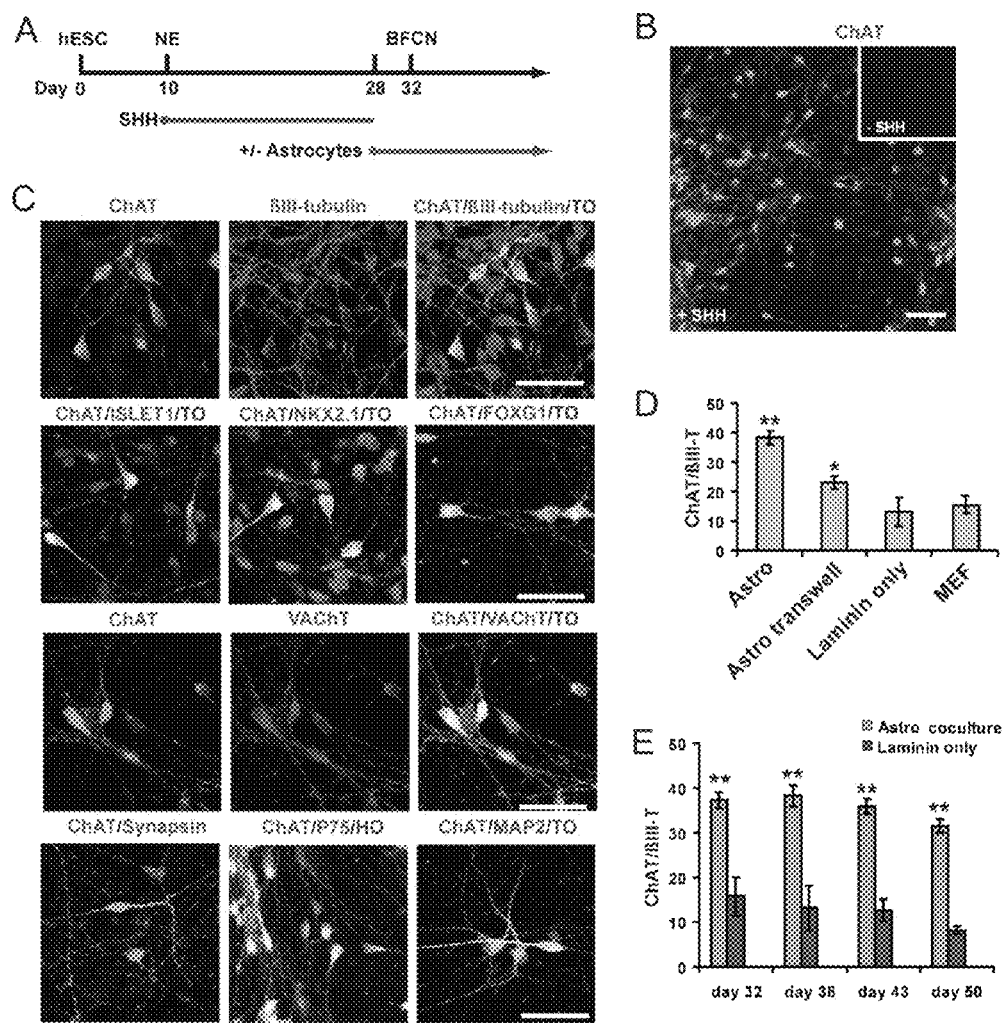
FIG. 2 shows differentiation of basal forebrain progenitors to BFCNs. (A) Schematic showing generation of BFCNs from basal forebrain progenitors in the presence of NGF and astrocytes. (B and C) 40% of the total βIII-tubulin+ neurons were ChAT+ cholinergic neurons. The ChAT+ neurons expressed additional neuronal (βIIItubulin, Map2, synapsin), cholinergic markers (VAChT, Islett P75), and regional markers (Nkx2.1, Islett FoxG1). Bar=50 µm. (D) Direct co-culture with astrocytes yielded the best proportion of ChAT+ neurons. (E) Persistent proportion of ChAT+ neurons when co-cultured with astrocytes.

Following the specification of MGE and POa/AEP-like progenitors, high concentration of SHH was removed from culture system at day 25 in order to promote cell cycle exit and neurogenesis. At the same time, nerve growth factor (NGF), a survival factor for cholinergic neurons (Gu et al., 2009; Hartikka and Hefti, 1988; Reilly et al., 2002), was added to the culture. The progenitors were dissociated and plated on laminin substrate or hESC-derived astrocytes (Krencik. R. et al., 2009) for differentiation (FIG. 2A).

Four days after plating (day 32), the majority of cells (90±2.3%) were process-bearing neurons, as revealed by positive immunostaining for βIII-tubulin. Among them, 14±2.5% were ChAT+ neurons (FIG. 2B, D). Most of the ChAT+ neurons were expressing Islett Nkx2.1, and FoxG1 (FIG. 2C), transcription factors that are associated with mature cholinergic neurons. Over time (by day 40), almost all the ChAT+ cells were also positive for the neurotrophin receptor P75, vesicular acetylcholine transporter (VAChT) that are associated with mature cholinergic neurons, as well as MAP2 and synapsin, proteins that are associated with mature neurons (FIG. 2C). Double immunostaining of ChAT with other neuronal type markers indicated that even though there were neurons that expressed Mash1, GABA, tyrosine hydroxylase (TH for dopaminergic neurons), Ctip2 (for striatal neurons), Ki67 (cell mitotic marker), the ChAT+ neurons were negative for those markers of major neuronal types in the ventral forebrain (not shown). Together, these results indicate that the cholinergic neurons generated in our culture system possess a ventral, forebrain, and mature neuronal identity. We name the cholinergic neurons generated in our culture system "basal forebrain cholinergic neurons (BFCNs).

Under the serum-free culture condition we described, there are few astrocytes in the first 8 weeks of hESC differentiation (Zhang et al., 2001). However, astrocytes are critical for survival and synaptogenesis of neurons (Johnson et al., 2007; Jordan et al., 2008; Ullian et al., 2001). We therefore examined whether astrocytes may support cholinergic neurons by plating the hESC-derived telencephalic progenitors onto a layer of astrocytes that were previously derived from hESCs (Krencik. R. et al., 2009) and plated at a low density (5,000 cells/cm2). Under this culture condition, 40% of total βIII-tubulin positive cells were ChAT+ BFCNs, significantly higher than the proportion (14±2.5%) of BFCNs in the absence of astrocytes (on laminin). This supporting effect appears to be contributed to both cell-cell contact and astrocyte-secreted factors as coculture of astrocytes in the transwell also increased the proportion of ChAT+ cells that were grown on laminin-coated coverslips albeit to a lesser degree than that in the cell-cell contact co-cultures (FIG. 2D). Furthermore, the proportion of ChAT+ BFCNs was constant in subsequent cultures when the cells were grown on astrocytes (FIG. 2E). Thus, co-culture with astrocytes significantly increases the population of ChAT+ BFCNs, possibly by promoting the survival of differentiated neurons.

Human ESC-Derived BFCNs are Electrophysiologically Active In Vitro

Figure 3:
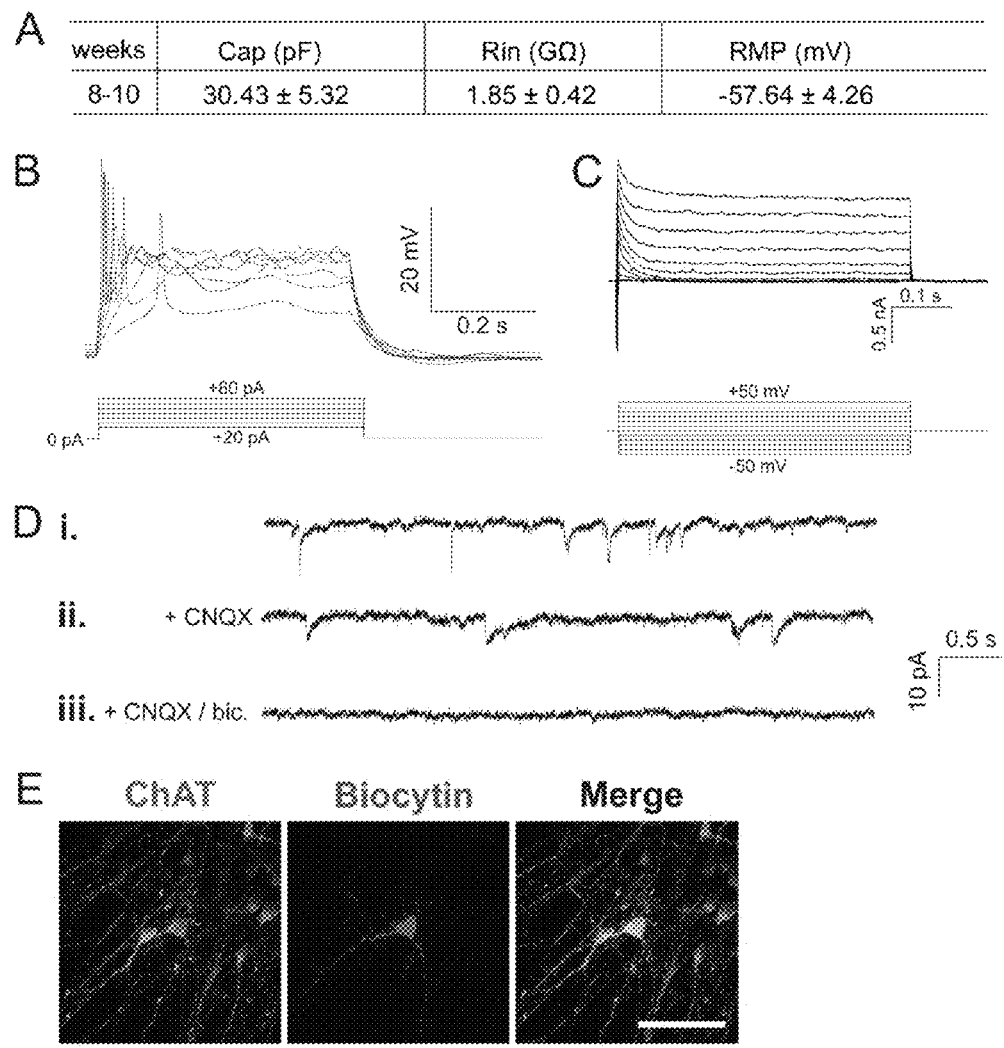
FIG. 3 shows that hESC-derived BFCNs are functional in vitro. (A) Electrophysiological characteristics of hESC-derived BFCNs which were differentiated for 8-10 weeks in vitro. (B) Action potentials were induced by +20 pA to +80 pA current injection into neurons. (C) Inward and outward currents were triggered upon −50 mV to 50 mV voltage steps; the amplified area showed the characteristic of Na+ current. (D) Spontaneous synaptic currents were recorded (i), and the AMPA receptor activity was blocked by CNQX (ii) and the GABA receptor activities were further eliminated by application of bicuculline on the base of CNQX (iii). (E) Immunocytochemistry showed that the recorded cells identified by biocytin were CHAT positive. Bar=50 µm.

To determine the functionality of the hESC-derived BFCNs, we first measured the electrophysiological properties of the BFCNs that were differentiated for 8-10 weeks by whole cell patch clamping recording (FIG. 3). We found that the mean cell capacitance was 30.43±5.32 pF, input resistance was 1.85±0.42 GΩ, and resting membrane potential was −57.64±4.26 mV (FIG. 3A). Action potentials were elicited by injection of current steps from +20 pA to +80 pA in all 12 neurons tested (FIG. 3B). Both inward Na+ and outward K+ currents (FIG. 3C) were observed in these cells by voltage clamp, indicating the maturation of ion channels responsible for the occurrence of action potentials. Spontaneous synaptic currents were observed, indicating that functional synaptic network has been formed with surrounding neurons (FIG. 3Di). The synaptic activity was partially blocked by CNQX and further eliminated by combination of CNQX and bicuculline (FIG. 3D ii, and iii), revealing both inhibitory (GABAergic) and excitatory (Glutamatergic) neurotransmission inputs. By the end of recording, biocytin was injected into recorded cells to determine the identity of neurons, and immunocytochemical analysis showed that 5 out of the 9 injected cells were positive for ChAT (FIG. 3E).

Grafted Human Cells Produce Cholinergic Neurons in Hippocampi

Figure 4:
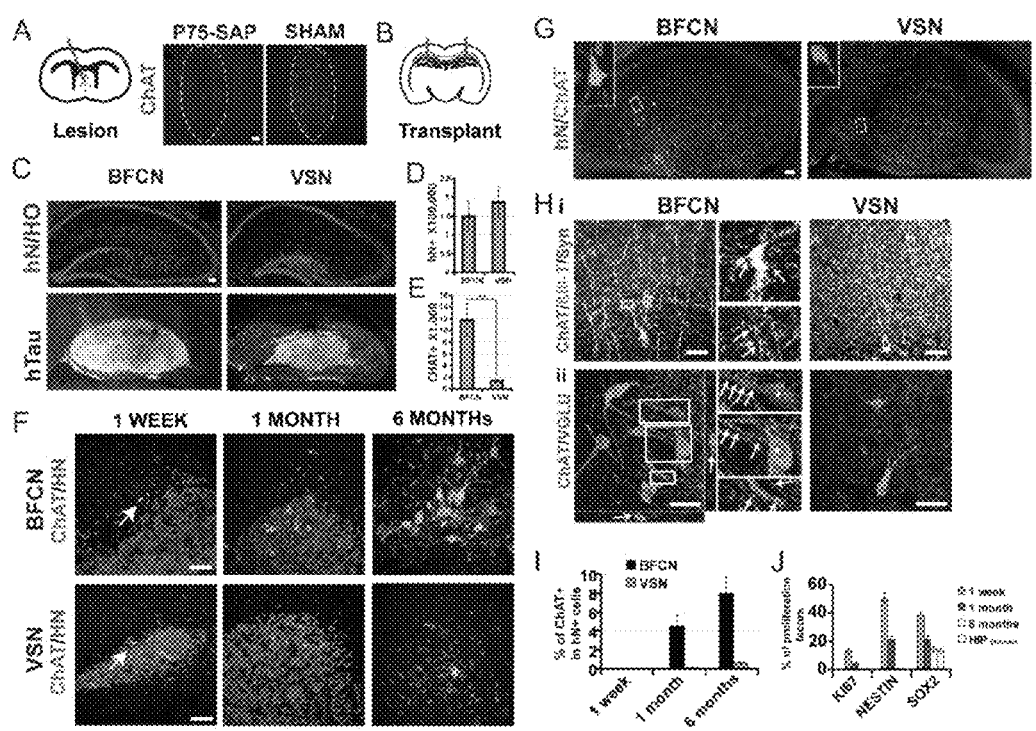
FIG. 4 shows that hESC-derived BFCNs survive and produce ChAT+ cholinergic neurons in hippocampi. (A and B) Schematic showing cholinergic lesion in the septum and cell transplantation into the hippocampus. (C, D and E) Both hESC-derived BFCN and spinal cholinergic neurons (VSN) survive, distribute, and grow hTau+ processes. Even though there are similar numbers of total grafted cells between the groups, the BFCN group contains substantially more ChAT+ cholinergic neurons. (F) ChAT+ cholinergic neurons are generated mostly from grafted progenitors as grafted ChAT+ cells hardly survive one week post-transplantation but new ChAT+ cells are produced later on. (G) The BFCN but not the spinal cholinergic group (VSN) produced large numbers of ChAT+ neurons in the grafted hippocampus. (H) The grafted BFCN but not spinal cholinergic neurons form synapses with hippocampal pyramidal neurons and receive glutamatergic inputs. (I) Stereological measurement estimates the total grafted human cells and those becoming ChAT+ cholinergic neurons. (J) Grafted human cells ceased proliferation by 6 months post-transplantation, as indicated by the lack of Ki67 staining.

To determine whether the in vitro produced human BFCNs function as cholinergic neurons in vivo, we generated a mouse model (n=30) of learning and memory loss by injecting anti-murine-p75-SAP, a specific immunotoxin which binds to low affinity neurotrophin receptors on BFCNs {{29 Berger-Sweeney, J. 2001; 31 Botly, L. C. 2009; 30 Walsh, T. J. 1996}}, to the medial septum of SCID mice (FIG. 4A). Cholinergic neurons in the medial septum, examined by immunostaining for ChAT two weeks after immunotoxin injection, were almost eliminated as compared to the sham surgery mice (n=10) that received only artificial cerebrospinal fluid (aCSF) injection (FIG. 4A).

Cholinergic lesion in the medial septum results in cholinergic denervation in the hippocampus, which underlies memory loss {{252 Woolf, N. J. 1991}}. We therefore transplanted to the hippocampi on both sides with BFCN that were differentiated from hESCs for 5 weeks without astrocyte co-culture (FIG. 4B). aCSF and ventral spinal neurons (VSNs) differentiated from the same hESCs for 5 weeks were injected to the same sites as controls. The VSNs, which contained 19±3.7% (n=3) of ChAT+ motor neurons and 20±4.6% (n=3) of GABAergic neurons before transplantation, were selected as a control for functional specificity of cholinergic neurons.

One week, one month and six months after transplantation, the grafted brains, with BFCNs or VSNs, exhibited no obvious difference in gross morphology from those that received only aCSF injection. DNA dye (Hoechst) staining on cross brain sections showed that the cell layer structures in the grafted hippocampus were maintained with the exception of injection sites (FIG. 4C). Immunostaining for human nuclei (hN) and human Tau (hTau) indicated that human cells were present in all grafted brains and distributed to the hippocampal proper with a preferential concentration in the dentate gyrus, resulting in a more enlarged dentate gyrus, especially in the injection site, or the center of the graft (FIG. 4C, G). Stereological measurement estimated that the total cell number (hN+) in an average BFCN graft was 150,167±40,010 and that in VSN graft was 186,894±40,919 at 6 months (FIG. 4D). ChAT cells were rarely observed in both groups in the first week post-transplantation (FIG. 4F). They increased in large numbers in the BFCN grafts over time and, to a much lesser degree, in the VSN group (FIG. 4F, I). By 6 months, there were 11,779±2783 ChAT+ cells in the BFCN graft whereas in grafts with VSNs there were 1,457±277 (FIG. 4E). Thus there was no obvious difference in graft cell numbers between the group with BFCNs and that with VSNs, but ChAT+ cells were significantly fewer (p<0.01) in the VSN grafts.

Human cholinergic neurons (ChAT+/hN+) in the BFCN grafts were mainly distributed along the pyramidal cell layer, although they were also scattered in other areas of the graft (FIG. 4G). In contrast, ChAT+ cells in the VSN grafts did not show clear preference (FIG. 4G). The ChAT cells also coexpressed the neuronal marker βIII-tubulin, as well as cholinergic markers VAChT and p75, and human-specific synaptophysin. It was noted that the ChAT-expressing cells in the BFCN graft increased substantially from 1 month post-graft and by 6 months, the average cell body area was 289.5±17.1 $\mu m^2$ as compared to 177.2±13.7 $\mu m^2$ for ChAT+ human cells in the VSN graft and 126.6±10.1 $\mu m^2$ for those in the medial septum.

Another feature of the grafted human BFCNs was that large numbers of fibers projected along the pyramidal layer, thus crossing the dendritic trees as well as cell bodies of the hippocampal pyramidal neurons. Confocal analysis revealed that the ChAT+ processes closely apposed to those of mouse pyramidal neurons and coexpressed human specific synaptophysin (FIG. 4Hi), suggesting formation of synaptic contact between human cholinergic neurons and mouse pyramidal neurons, most of which are glutamatergic neurons {{244 Francis, P. T. 2003}}. In contrast, there were few ChAT+ fibers along the pyramidal layer in the VSN grafts, but similar numbers of human synaptophysin+ puncta were observed (FIG. 4Hi). Furthermore, cholinergic neurons in BFCN grafts (FIG. 4H ii), but rarely in VSN grafts (FIG. 4H ii), were surrounded and overlapped with puncta of vesicular glutamate transporter (vGLU), suggesting glutamatergic inputs from endogenous brain areas such as the hippocampus and thalamus. It should be noted that BFCNs grafts were void of glutamatergic neurons (data not shown). Thus, BFCNs, but not spinal cholinergic neurons, appear to synaptically integrate into neural circuitries in the mouse brain.

Transplantation of hESC derivatives is often associated with overgrowth from precursor cells. Examination of grafts at 1 week post-transplantation revealed that 13±1.8% of human cells (hN+) were KI67+, 52±3.3% were NESTIN+, and 39±2.6% were SOX2+ (FIG. 4J), but none were positive for pluripotent factors NANOG or OCT3/4 (data not shown). By 1 month post transplantation, KI67+ cells decreased to 3.8±0.7%, NESTIN+ cells were 21±2.7%, and SOX2+ cells were 21±3.4% (FIG. 4J). After 6 months of transplantation, KI67+ cells (<0.01%) were rarely found in the grafts, less than 1% cells expressed NESTIN, and SOX2+ cells were 14±1.9% (FIG. 4J), similar to the expression level in adult mouse hippocampus {{251 Jinno, S. 2011}}. Over time, the human cells dispersed throughout the hippocampus (FIG. 4F). The vast majority of grafted cells become post-mitotic, with 74.3±1.5% βIII-tubulin+ neurons and 11.7±1.0% GFAP+ astrocytes in the BFCN grafts and 73.6±0.7% βIII-tubulin+ and 12.9±2.5% GFAP+ cells in the VSN grafts.

Figure 5:
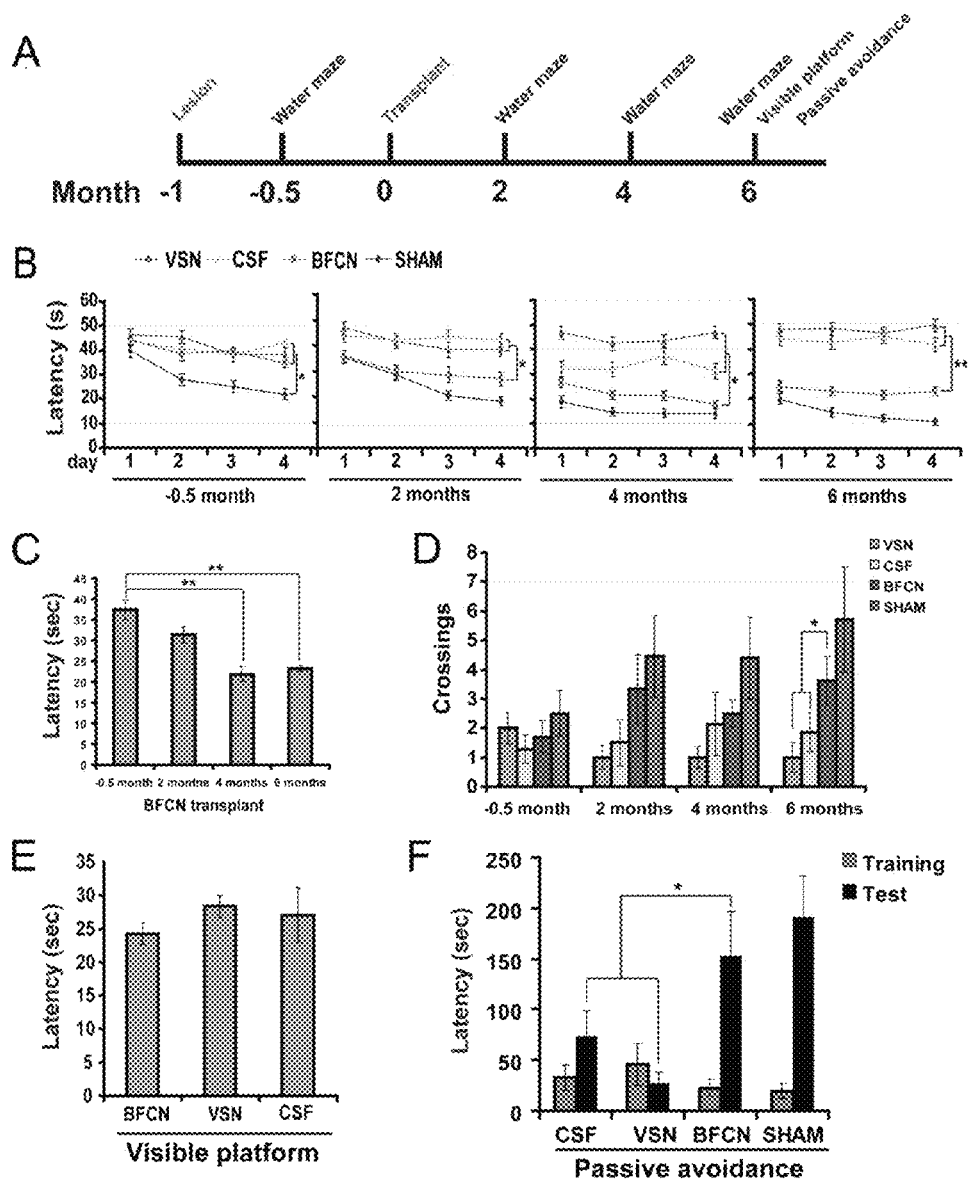
FIG. 5 shows that Transplantation of hESC-derived BFCNs, but not spinal cholinergic neurons, corrects learning and memory deficits. (A) Schematic indicating the behavioral schedule of experimental animals. (B) Morris water maze tests show decreased latency in finding the platform for animals that received BFCN transplant and those that do not have lesion (sham). (C) Time course of behavioral changes following BFCN transplantation. (D) The times crossing the removed platform were increased in the BFCN-transplanted group as compared to controls 6 months after transplantation. (E) All animals from the three transplanted groups showed a similar latency in landing on the visible platform. (F) Animals with BFCN transplants showed a longer latency than those with VSN or CSF injections in passive avoidance tests. *p<0.05, **p<0.01.

Transplantation of hESC-Derived BFCNs Contributes to Behavioral Improvement in Mice Synaptic connections between BFCNs and the hippocampus are associated with learning and memory. Morris water maze tests showed that the lesioned mice displayed drastically increased time (p<0.05) to reach a hidden platform as compared to a sham group 2 weeks post-lesion (FIG. 5A, B). The BFCN-transplanted mice began to show a decreased latency in identifying the platform as compared to the VSN- and aCSF-injected mice 2 months post-transplantation (FIG. 5B). The trend was statistically significant by 4 and 6 months (p<0.05 and p<0.01, respectively) after transplantation (FIG. 5B, C). As a parallel test, the BFCN group crossed the removed platform more often than the two controls, especially at the $6^{th}$ month (p<0.05) (FIG. 5D). Visible platform water maze tests revealed that all transplanted mice had a similar latency in landing on the platform (FIG. 5E), validating that the different water maze behaviors are not caused by variations in motor skills nor vision. Another test for short-term memory, passive avoidance, indicated that BFCN-grafted animals had a similarly increased latency as sham mice to enter a dark compartment where they received a shock 24 hours ago, whereas control mice (aCSF and VSN groups) had a significantly shorter latency (p<0.05) (FIG. 5F). Thus the in vitro produced human BFCNs, but not VSNs, ameliorate deficits in learning, memory, and spatial cognition of mice with a septal cholinergic lesion.

LGE-like Progenitors Generate DARPP32-Expressing Medium Spiny GABA Neurons

Figure 6:
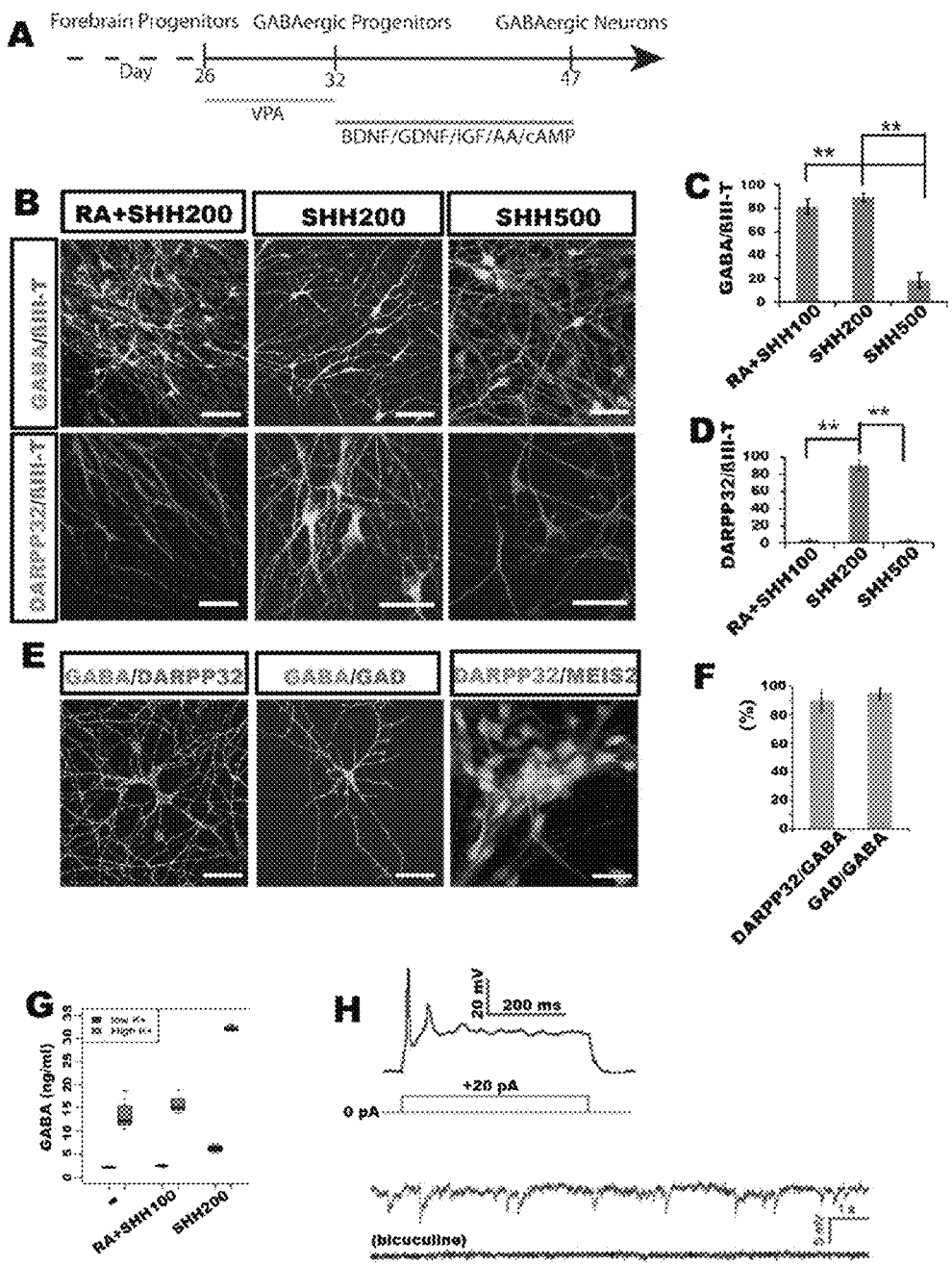
FIG. 6 shows differentiation and characterization of GABA neurons. (A) Schematic of the procedure of differentiation from progenitors into GABA neurons. (B, C and D) While GABA neurons are efficiently generated in the presence of low (200 ng/ml) or high (500 ng/ml) concentration of SHH (or purmorphamine) or under both retinoic acid (RA) and SHH, on the culture with low concentration of SHH generated GABA neurons that express the striatal medium spiny GABA neuron marker DARPP32 and the efficiency is about 87% of tubulin+ neurons. (E, F and G) These GABA neurons express additional markers, including GAD65/67 and Meis2, showing extensive dendritic trees and spines. (G) HPLC measurement of GABA release from glutamatergic neurons (control), spinal neurons and medium spiny GABA projection neurons under base and high-potassium (50 mM, 3 min) conditions. Data are means±SEM of five wells. *p<0.05, One way ANOVA. Scale bars: 50 µm. (H) Electrophysiological analysis indicated that hESC-derived GABA neurons fire action potentials and display spontaneous synaptic Currents which were eliminated by application of bicuculin, a GABA receptor blocker.

Following the specification of LGE-like progenitors, the progenitor cultures in suspension were exposed to valproic acid (VPA, Sigma) without SHH or purmorphamine for 6 days before they were dissociated to single cells with accutase and plated onto laminin substrate for neuronal differentiation at day 32 (FIG. 6A). Neurotrophic factors, brain-derived neurotrophic factor (BDNF), glial cell line derived neurotrophic factor (GDNF), and insulin-like growth factor (IGF-1) were added at day 32 to promote cell cycle exit and neurogenesis (FIG. 6A). 15 days after plating (day 47), the majority of cells (93.2%±3.56%) were process-bearing neurons, as revealed by phase contrast and by positive immunostaining for Tuj1 (FIG. 6B, C). Most of them are medium sized neurons with large and extensive dendritic trees packed with numerous small spines (FIG. 6B, E). Immunostaining revealed that 75.8%±2.19% of the cells were positive for GABA and 80.1%±5.89% for DARPP32 (FIGS. 6D, E, and J), two major GABAergic markers. There were few positive for choline acetyltransferase (ChAT) (1.2%±0.78% I). Many GABA neurons were also positive for Meis 2 (FIG. 6E), a striatal transcription factor (Parmar et al., 2002) and GAD65/67 (FIG. 6E), an enzyme required for GABA synthesis. Importantly, almost all of the GABA neurons were positive for DARPP32 (89.7%±8.31%, FIG. 6H). In contrast, GABA neurons were also generated in the presence of high concentration of SHH or both SHH and RA, few of the GABA neurons carry striatal markers, DARPP32 or Meis2 (FIG. 6B). Together, these results suggest that the GABA neurons generated in our culture system possess striatal projection neuronal phenotypes. We therefore name these GABA neurons "medium spiny GABA projection neurons".

HPLC measurement of media conditioned by the hESC-derived medium spiny GABA projection neurons (day 90) showed that these cultures released measurable amount of GABA whereas neurons differentiated from hESCs without SHH treatment, which are primarily glutamatergic neurons and some GABA neurons, or those differentiated in the presence of RA and purmorphamine, which generated ventral spinal neurons including motor neurons and some GABA neurons, produced much lower concentration of GABA (baseline 2.47 ng/ml and high K+ 13.87 ng/ml). Stimulation of the cultures with a high-potassium solution, which depolarizes neurons, resulted in increased GABA release in all the cultures over the same period, most notably in the medium spiny GABA projection neuron cultures with over 10-fold increase (FIG. 6G). These results further confirm the identity of GABAergic neurons in the cultures that were treated with SHH (or purmorphamine) and VPA.

To determine the functionality of the hESC-derived medium spiny GABA projection neurons, we first measured the electrophysiological properties of the medium spiny GABA projection neurons that were differentiated for 70 days by whole cell patch clamping recording. We found that the mean cell capacitance was 27.73±4.29 pF, input resistance was 2.31±0.56 GΩ, and resting membrane potential was 42.96±2.87 mV. Action potentials were elicited by injection of current steps from +20 nA to +80 nA in 16 neurons tested (FIG. 6H). Both inward Na+ and outward K+ currents were observed in these cells by voltage clamp, indicating the maturation of ion channels responsible for the occurrence of action potentials. Spontaneous synaptic currents were observed, indicating that functional synaptic network has been formed with surrounding neurons (FIG. 6H). The synaptic activity was nearly completely blocked by bicuculline (FIG. 6H), revealing primarily inhibitory (GABAergic) neurotransmission inputs. By the end of recording, biocytin was injected into recorded cells to confirm the identity of neurons, which were GABA positive by immunocytochemistry (16 GABA+/18 biocytin-labeled).

Transplantation of hESC-Derived Medium Spiny GABA Projection Neurons Contributes to Behavioral Improvement in Mice To assess the function of in vitro produced human medium spiny GABA projection neurons, we created a unilateral QA-induced striatal lesion model in immune deficient SCID mice (Sanberg et al., 1989; Reynolds et al., 2006). Four weeks post injection of QA, majority of neurons, as labeled by NeuN, including FoxP2 and DARPP32 expressing GABA projection neurons in the striatum were lost, resulting in a smaller striatum in the lesion side as compared to the non-lesion side. Accompanying the loss of neurons, there was a significant increased level of GFAP expression in astrocytes. Treadscan analysis showed that the lesioned mice had a longer stride length on the right limbs than the control animals that received aCSF injection.

hESC-derived medium spiny GABA projection neuron were transplanted into the lesioned striatum 6-8 weeks following the lesion of 8 mice. To determine whether functional recovery of the model depends on specific types of GABA neurons, we also transplanted into 8 mice GABA neurons that were differentiated from hESCs in the presence of RA and SHH, which exhibited spinal but not striatal phenotypes. One week after transplantation, grafted human cells were present in brains that received medium spiny GABA projection neurons or spinal neurons, as revealed by Hoechst staining. They were mostly nestin positive progenitors.

Figure 7:
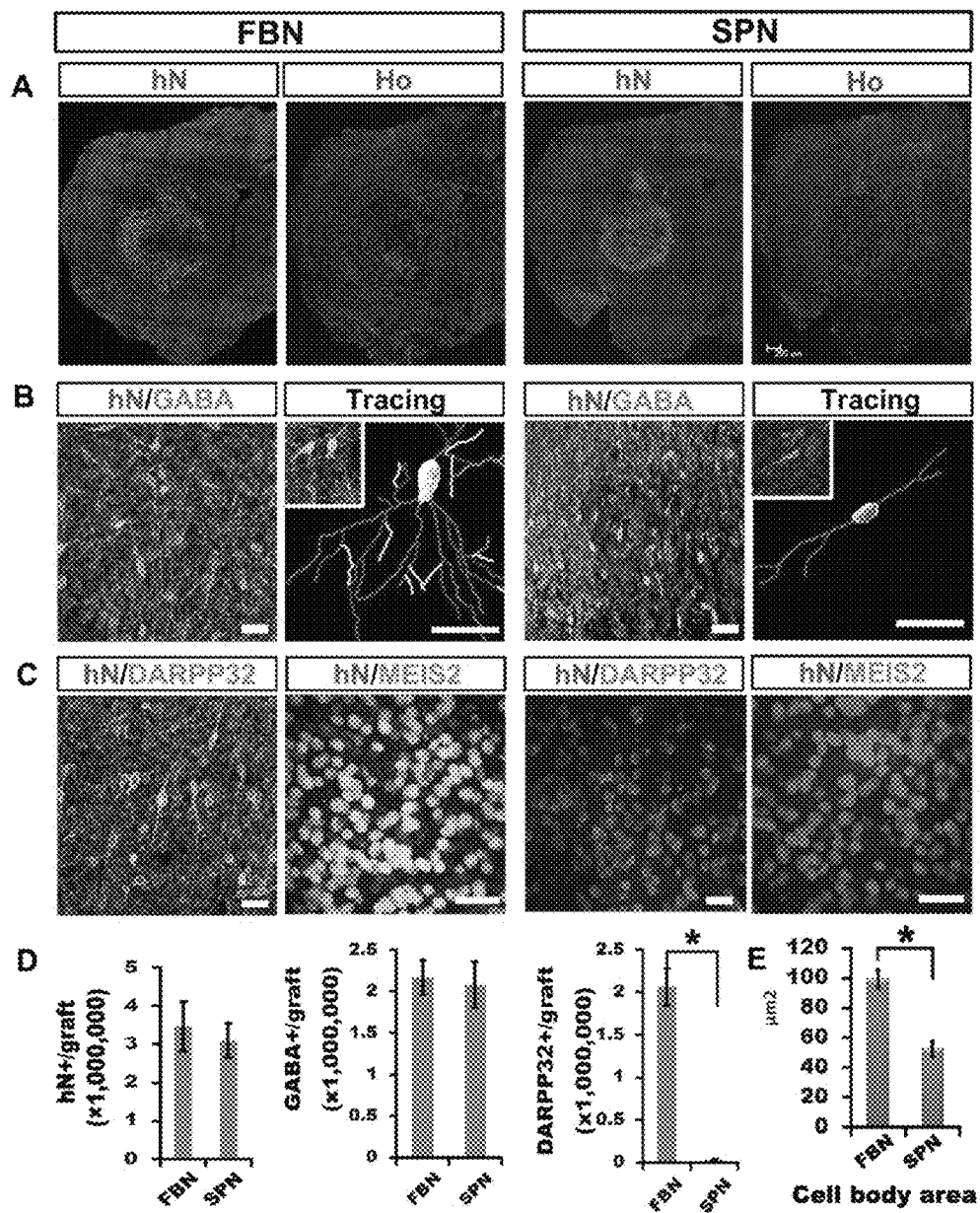
FIG. 7 shows transplantation of hESC/iPSC-derived stiatal and spinal GABA neurons in the brain of mouse model of Huntington disease. (A) Both types of neurons survived in the mouse brain. (B and C) Only the hESC-derived striatal GABA neurons, but not the spinal GABA neurons, produce projection neurons with complex neurites, and express DARPP32 and Meis2. (D) Stereological analysis indicated that there are similar numbers of total grafted cells, total number of GABA neurons, but the GABA neurons in the forebrain neuron group (FBN) are large in size and express DARP32.

Four months after transplantation, the grafted brain, with medium spiny GABA projection neurons or spinal GABA neurons, exhibited no obvious difference in gross morphology from those without transplant. Coronal sections of the brain showed presence of grafts in all the transplanted animals. Immunostaining for human nuclei protein (hNu) indicated that the human cells are primarily distributed to the striatum (FIG. 7A). Stereological measurement estimated the total cell number (hNu) in each graft to range from 363,446 to 719,433, with an average of 541,439. There was no difference in graft size between transplanting medium spiny GABA projection neurons and spinal GABA neurons (FIG. 7D).

In the grafts with both types of GABA neurons, a large proportion of human cells were positive for GABA [FIG. 7B]. However, the GABA neurons in the graft with medium spiny GABA neuron transplant (FBN) are larger with more complex processes than that with the spinal GABA neurons (SPN) [FIG. 7B, E]. Furthermore, the GABA neurons in the FBN group, but not the SPN group, express DARPP32 and Meis2 [FIG. 7C]. Taken together, although both types of GABA neurons survived transplantation (FIG. 7D), only the forebrain medium spiny GABA neurons generate striatal projection GABA neurons, which corresponds to the behavioral improvement in those animals.

Figure 8:
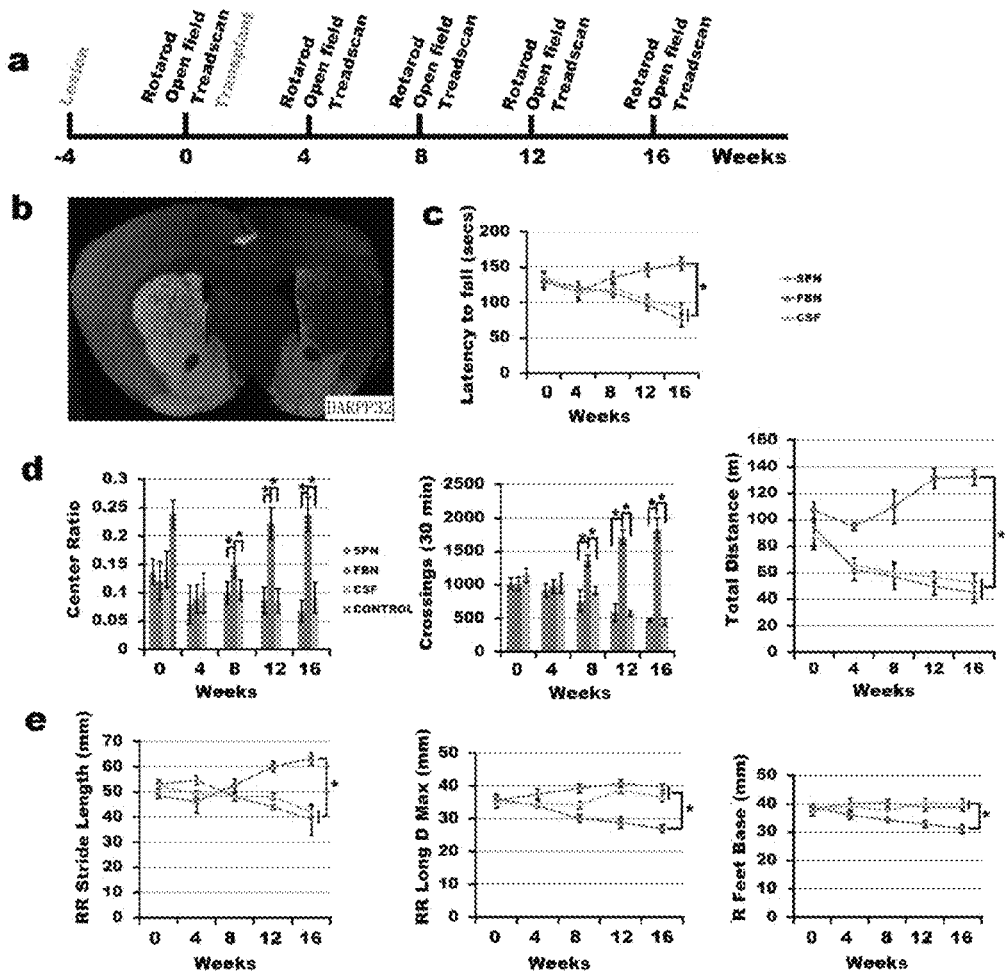
FIG. 8 shows that transplantation of hESC/iPSC-derived forebrain, but not the spinal, GABA neurons corrects locomotion deficits in Huntington's mice. (A) Schematic diagram showing procedures of behavioral analysis. (B) DARPP32 staining shows the loss of DARPP32-expressing GABA neurons in the striatum of Huntington mice. (C) Rotarod test shows increased latency to fall from the rotating rod after transcription with forebrain GABA neurons (FBN). (D) Field test shows significantly improved central ratio and crossing by mice that received FBN transplantation. (E) Treadscan analysis, which examines fine limb movements, showed that mice with forebrain GABA neuron transplantation had a shorter stride length than those with spinal GABA neurons or aCSF injection.
Figure 9:
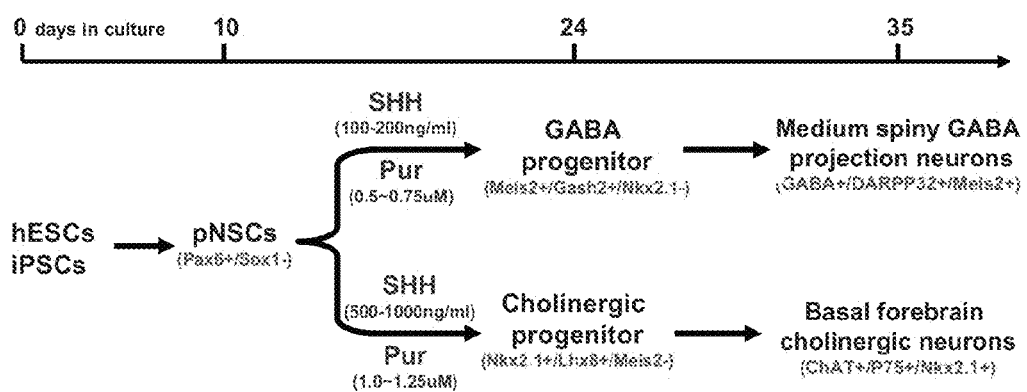
FIG. 9 is a diagram summarizing the conversion of primate pluripotent stem cells, preferably hESCs or iPSCs, to a nearly homogeneous population of Nkx2.1-expressing, MGE and AEP/POa-like progenitors or Meis2-expressing LGE-like progenitors disclosed in the present application.

Unilateral QA-induced striatal lesion resulted in locomotion deficits typical of HD, including decreased latency in rotarod test, decrease in center ratio/crossings in open field test, and changes in a number of parameters of fine gait movements revealed by Treadscan such as smaller stride length but a larger foot base (distances between front and rear foot pair), increased minimum lateral deviation of limbs, increased longitudinal deviation of rear limbs and diagonal coupling of these limbs (FIG. 8). The small stride length, lagging and wobbling of rear limbs resemble the gait abnormalities seen in typical HD patients.

Monthly Behavioral analysis [FIG. 8A] post-transplantation revealed that mice receiving the forebrain but not spinal GABAergic neuron transplantation exhibited increased latency on rotarod and center ratio/crossings in open field tests (FIG. 8C). Open field analysis indicated an increase central ratio and crossing times (FIG. 8D). Gait analysis with Treadscan indicated that in mice that received forebrain GABA neurons, the maximum longitudinal deviation of their rear limbs, especially on the right side, became smaller over time. A similar improvement was also observed in minimum longitudinal deviation of the front left limbs. Mice receiving transplantation of spinal GABAergic neurons showed similar effects as their forebrain counterparts in recovering the minimum longitudinal deviation of the front left limb, but fail to do the same job on the rear limbs. Rather, they seem to alter the maximum longitudinal deviation of the rear right limb to an opposite direction from normal (FIG. 8D). These results indicate that the forebrain but not spinal GABAergic neurons correct the locomotion deficits in the QA-lesioned mice.

REFERENCE LIST

Backman, C., Rose, G. M., Hoffer, B. J., Henry, M. A., Bartus, R. T., Friden, P., and Granholm, A. C. (1996). Systemic administration of a nerve growth factor conjugate reverses age-related cognitive dysfunction and prevents cholinergic neuron atrophy J. Neurosci. 16, 5437-5442.

Berger-Sweeney, J., Stearns, N. A., Murg, S. L., Floerke-Nashner, L. R., Lappi, D. A., and Baxter, M. G. (2001). Selective immunolesions of cholinergic neurons in mice: effects on neuroanatomy, neurochemistry, and behavior J. Neurosci. 21, 8164-8173.

Botly, L. C., and De Rosa, E. (2009). Cholinergic deafferentation of the neocortex using 192 IgG-saporin impairs feature binding in rats J. Neurosci. 29, 4120-4130.

Du, T., Xu, Q., Ocbina, P. J., and Anderson, S. A. (2008). NKX2.1 specifies cortical interneuron fate by activating Lhx6 Development 135, 1559-1567.

Du, Z. W., Hu, B. Y., Ayala, M., Sauer, B., and Zhang, S. C. (2009). Cre recombination-mediated cassette exchange for building versatile transgenic human embryonic stem cells lines Stem Cells 27, 1032-1041.

Flames, N., Pla, R., Gelman, D. M., Rubenstein, J. L., Puelles, L., and Mann, O. (2007). Delineation of multiple subpallial progenitor domains by the combinatorial expression of transcriptional codes J. Neurosci. 27, 9682-9695.

Fragkouli, A., van Wijk, N. V., Lopes, R., Kessaris, N., and Pachnis, V. (2009). LIM homeodomain transcription factor-dependent specification of bipotential MGE progenitors into cholinergic and GABAergic striatal interneurons Development 136, 3841-3851.

Furusho, M., Ono, K., Takebayashi, H., Masahira, N., Kagawa, T., Ikeda, K., and Ikenaka, K. (2006). Involvement of the Olig2 transcription factor in cholinergic neuron development of the basal forebrain Dev. Biol. 293, 348-357.

Gu, H., Long, D., Song, C., and Li, X. (2009). Recombinant human NGF-loaded microspheres promote survival of basal forebrain cholinergic neurons and improve memory impairments of spatial learning in the rat model of Alzheimer's disease with fimbria-formix lesion Neurosci. Lett. 453, 204-209.

Hartikka, J., and Hefti, F. (1988). Development of septal cholinergic neurons in culture: plating density and glial cells modulate effects of NGF on survival, fiber growth, and expression of transmitter-specific enzymes J. Neurosci. 8, 2967-2985.

Hu, B. Y., and Zhang, S. C. (2009). Differentiation of spinal motor neurons from pluripotent human stem cells Nat. Protoc. 4, 1295-1304.

Johnson, M. A., Weick, J. P., Pearce, R. A., and Zhang, S. C. (2007). Functional neural development from human embryonic stem cells: accelerated synaptic activity via astrocyte coculture J. Neurosci. 27, 3069-3077.

Jordan, P. M., Cain, L. D., and Wu, P. (2008). Astrocytes enhance long-term survival of cholinergic neurons differentiated from human fetal neural stem cells J. Neurosci. Res. 86, 35-47.

Krencik. R., Weick J. H., and Z. Zhang & S. C. Zang. (2009). Regional and functional specific astrocytes from human embryonic stem cells. Society for Neuroscience Abstract 808.9, LaVaute, T. M., Yoo, Y. D., Pankratz, M. T., Weick, J. P., Gerstner, J. R., and Zhang, S. C. (2009). Regulation of neural specification from human embryonic stem cells by BMP and FGF Stem Cells 27, 1741-1749.

Lee, S. H., Lumelsky, N., Studer, L., Auerbach, J. M., and McKay, R. D. (2000). Efficient generation of midbrain and hindbrain neurons from mouse embryonic stem cells Nat. Biotechnol. 18, 675-679.

Li, X. J., Du, Z. W., Zarnowska, E. D., Pankratz, M., Hansen, L. O., Pearce, R. A., and Zhang, S. C. (2005). Specification of motoneurons from human embryonic stem cells Nat. Biotechnol. 23, 215-221.

Li, X. J., Zhang, X., Johnson, M. A., Wang, Z. B., Lavaute, T., and Zhang, S. C. (2009). Coordination of sonic hedgehog and Wnt signaling determines ventral and dorsal telencephalic neuron types from human embryonic stem cells Development 136, 4055-4063.

Manabe, T., Tatsumi, K., Inoue, M., Matsuyoshi, H., Makinodan, M., Yokoyama, S., and Wanaka, A. (2005). L3/Lhx8 is involved in the determination of cholinergic or GABAergic cell fate J. Neurochem. 94, 723-730.

Manuel, M., Martynoga, B., Yu, T., West, J. D., Mason, J. O., and Price, D. J. (2010). The transcription factor Foxg1 regulates the competence of telencephalic cells to adopt subpallial fates in mice Development 137, 487-497.

Mesulam, M. M., Mufson, E. J., Wainer, B. H., and Levey, A. I. (1983). Central cholinergic pathways in the rat: an overview based on an alternative nomenclature (Ch1-Ch6) Neuroscience 10, 1185-1201.

Perrier, A. L., Tabar, V., Barberi, T., Rubio, M. E., Bruses, J., Topf, N., Harrison, N. L., and Studer, L. (2004). Derivation of midbrain dopamine neurons from human embryonic stem cells Proc. Natl. Acad. Sci. U.S.A. 101, 12543-12548.

Peterson, D. A. (1999). Quantitative histology using confocal microscopy: implementation of unbiased stereology procedures Methods 18, 493-507.

Puelles, L., Kuwana, E., Puelles, E., Bulfone, A., Shimamura, K., Keleher, J., Smiga, S., and Rubenstein, J. L. (2000). Pallial and subpallial derivatives in the embryonic chick and mouse telencephalon, traced by the expression of the genes Dlx-2, Emx-1, Nkx-2.1, Pax-6, and Tbr-1 J. Comp. Neurol. 424, 409-438.

Reilly, J. O., Karavanova, I. D., Williams, K. P., Mahanthappa, N. K., and Allendoerfer, K. L. (2002). Cooperative effects of Sonic Hedgehog and NGF on basal forebrain cholinergic neurons Mol. Cell. Neurosci. 19, 88-96.

Roy, N. S., Cleren, C., Singh, S. K., Yang, L., Beal, M. F., and Goldman, S. A. (2006). Functional engraftment of human ES cell-derived dopaminergic neurons enriched by coculture with telomerase-immortalized midbrain astrocytes Nat. Med. 12, 1259-1268.

Singh Roy, N., Nakano, T., Xuing, L., Kang, J., Nedergaard, M., and Goldman, S. A. (2005). Enhancer-specified GFP-based FACS purification of human spinal motor neurons from embryonic stem cells Exp. Neurol. 196, 224-234.

Ullian, E. M., Sapperstein, S. K., Christopherson, K. S., and Barres, B. A. (2001). Control of synapse number by glia Science 291, 657-661.

Walsh, T. J., Herzog, C. D., Gandhi, C., Stackman, R. W., and Wiley, R. G. (1996). Injection of IgG 192-saporin into the medial septum produces cholinergic hypofunction and dose-dependent working memory deficits Brain Res. 726, 69-79.

Wilson, S. W., and Rubenstein, J. L. (2000). Induction and dorsoventral patterning of the telencephalon Neuron 28, 641-651.

Winkler, J., Thal, L. J., Gage, F. H., and Fisher, L. J. (1998). Cholinergic strategies for Alzheimer's disease J. Mol. Med. 76, 555-567.

Winn, S. R., Lindner, M. D., Lee, A., Haggett, G., Francis, J. M., and Emerich, D. F. (1996). Polymer-encapsulated genetically modified cells continue to secrete human nerve growth factor for over one year in rat ventricles: behavioral and anatomical consequences Exp. Neurol. 140, 126-138.

Yan, Y., Yang, D., Zarnowska, E. D., Du, Z., Werbel, B., Valliere, C., Pearce, R. A., Thomson, J. A., and Zhang, S. C. (2005). Directed differentiation of dopaminergic neuronal subtypes from human embryonic stem cells Stem Cells 23, 781-790.

Yang, D., Zhang, Z. J., Oldenburg, M., Ayala, M., and Zhang, S. C. (2008). Human embryonic stem cell-derived dopaminergic neurons reverse functional deficit in parkinsonian rats Stem Cells 26, 55-63.

Zhang, S. C. (2006). Neural subtype specification from embryonic stem cells Brain Pathol. 16, 132-142.

Zhang, S. C., Wernig, M., Duncan, I. D., Brustle, O., and Thomson, J. A. (2001). In vitro differentiation of transplantable neural precursors from human embryonic stem cells Nat. Biotechnol. 19, 1129-1133.

Zhao, Y., Mann, O., Hermesz, E., Powell, A., Flames, N., Palkovits, M., Rubenstein, J. L., and Westphal, H. (2003). The LIM-homeobox gene Lhx8 is required for the development of many cholinergic neurons in the mouse forebrain Proc. Natl. Acad. Sci. U.S.A. 100, 9005-9010.

---

We claim:

1. A method of creating a population of GABA projection neurons comprising the steps of
   a) culturing primate pluripotent stem cells under serum-free conditions to obtain Pax6+/Sox1⁻ primitive neural stem cells;
   b) culturing the Pax6⁺/Sox1⁻ primitive neural stem cells to in the presence of 100-200 ng/ml Sonic Hedgehog (SHH) or 0.5-0.75 µM purmorphamine to obtain a cell population comprising at least 80% Meis2⁺/Gsh2⁺/Nkx2.1⁻ GABA progenitors, and
   c) culturing the GABA progenitors in the presence of valproic acid (VPA) and neurotrophic factors selected from the group consisting of brain derived neurotrophic factor (BDNF), glial-derived neurotrophic factors (GDNF), insulin-like growth factor (IGF1), and cyclic AMP (cAMP) to obtain a cell population comprising at least 70% GABK⁺/DARPP32⁺/Meis2⁺ GABA projection neurons.

2. The method of claim 1 wherein the primate pluripotent stem cells are human cells.

3. The method of claim 1 wherein at least 70% of the cultured GABA progenitors differentiate into GABA⁺/DARPP32⁺/Meis2⁺ striatal GABA projection neurons.

4. The method of claim 1 wherein the cell population of (c) comprises at least 80% GABA+/DARPP32+/Meis2+GABA projection neurons.

5. The method of claim 1 wherein at least 80% of the cell population of step (b) are GABA progenitors.

6. The method of claim 1 wherein at least 90% of the cell population of step (b) are GABA progenitors.

7. A method of creating a population of basal forebrain cholinergic neurons (BFCNs), comprising the steps of:
   a) culturing primate pluripotent stem cells under serum-free conditions to obtain Pax6+/Sox1⁻ primate neural stem cells;
   b) culturing the primate neural stem cells in the presence of 500-1000 ng/ml SHH or 1.0-1.25 µM purmorphamine to obtain a cell population comprising at least 90% Nkx2.1⁺/Lhx8⁺/Meis2⁻ cholinergic progenitors; and
   c) culturing the cholinergic progenitors in the presence of nerve growth factor (NGF) to obtain a cell population comprising at least 30% ChAT⁺/p75⁺/Nkx2.1⁺ BFCNs.

8. The method of claim 7 wherein the primate pluripotent stem cells are human cells.

9. The method of claim 7 wherein the cholinergic progenitors are cultured in the presence of astrocytes.

10. The method of claim 7 wherein at least 30% of the cultured cholinergic progenitors differentiate into ChAT⁺/p75⁺/Nkx2.1⁺ BFCNs.

11. The method of claim 7 wherein the cell population of (c) comprises at least 40% ChAT⁺/p75⁺/Nkx2.1⁺ BFCNs.

12. The method of claim 7 wherein at least 90% of the cell population of step (b) are GABA progenitors.

13. The method of claim 7 wherein the cell population of (b) comprises at least 95% Nkx2.1⁺/Lhx8⁺/Meis2⁻ cholinergic progenitors.

* * * * *

UNITED STATES PATENT AND TRADEMARK OFFICE
CERTIFICATE OF CORRECTION

PATENT NO. : 8,895,302 B2
APPLICATION NO. : 13/207202
DATED : November 25, 2014
INVENTOR(S) : Su-Chun Zhang et al.

It is certified that error appears in the above-identified patent and that said Letters Patent is hereby corrected as shown below:

In The Specification

Column 3, line 31   -   "Islett" should be --Islet1--

Column 3, line 32   -   "Islett" should be --Islet1--

Column 7, line 5    -   "Islett" should be --Islet1--

Column 14, line 62  -   "Islett" should be --Islet1--

Column 29, line 16  -   "cells to" should be --cells--

In The Claims

Column 29, line 27  -   "GABK$^+$/DARPP32$^{+/}$Meis2$^+$" should be --GABA$^+$/DARPP32$^+$/Meis2$^+$--

Signed and Sealed this
Sixteenth Day of August, 2016

Michelle K. Lee
*Director of the United States Patent and Trademark Office*

SEQUENCE LISTING

```
<160> NUMBER OF SEQ ID NOS: 21

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
ttcaatggga gagggagagt gctt                                             24
```

```
<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 2
ccgtcagcct ttgtgaatgg tgtt                                              24

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
acagatctac gccagcgact                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
catggtgtcg tagtggatgc                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
gtctcccggg gattttgtat                                                   20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
tctccatctt ggcagagctt                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
ccaaaaccag caaaaagagc                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 8
tggcgtgctc tacaattctg                                               20

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
ttcttgctga agccgatgc                                                19

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
cgcatccaat ctcaaggaat                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
cagagtgtgc ccagagtgaa                                               20

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12
tctttgcttg ggaaatccg                                                19

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 13
ctgcccgttc aacatcctta g                                             21

<210> SEQ ID NO 14
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 14
ggtaagtgcg caatgctaag ctgt                                          24
```

```
<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 15
tacaaagccc agtttgcaac gcag                                          24

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
tcgacagtca gccgcatctt cttt                                          24

<210> SEQ ID NO 17
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 17
accaaatccg ttgactccga cctt                                          24

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 18
atgtcgctcc ttctatgtc                                                19

<210> SEQ ID NO 19
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 19
tcactatccg aatttcaggc tca                                           23

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
atgtcgcgct ccttctatgt c                                             21

<210> SEQ ID NO 21
<211> LENGTH: 21
<212> TYPE: DNA
<213> ORGANISM: Artificial Sequence
```

```
<220> FEATURE:
<223> OTHER INFORMATION: Synthetic oligonucleotide

<400> SEQUENCE: 21
atgccaagcg ggatgaagaa a                                              21
```